US012714690B2

(12) United States Patent
Xu et al.

(10) Patent No.: US 12,714,690 B2
(45) Date of Patent: Aug. 25, 2026

(54) PH-RESPONSIVE LIPIDOID NANOPARTICLES FOR INTRACELLULAR MRNA DELIVERY

(71) Applicant: Trustees of Tufts College, Boston, MA (US)

(72) Inventors: Qiaobing Xu, Lexington, MA (US); Yamin Li, Somerville, MA (US)

(73) Assignee: Trustees of Tufts College, Medford, MA (US)

( * ) Notice: Subject to any disclaimer, the term of this patent is extended or adjusted under 35 U.S.C. 154(b) by 716 days.

(21) Appl. No.: 18/009,102

(22) PCT Filed: Jun. 10, 2021

(86) PCT No.: PCT/US2021/036819

§ 371 (c)(1),
(2) Date: Dec. 8, 2022

(87) PCT Pub. No.: WO2021/252769

PCT Pub. Date: Dec. 16, 2021

(65) Prior Publication Data

US 2023/0321036 A1 Oct. 12, 2023

Related U.S. Application Data

(60) Provisional application No. 63/038,451, filed on Jun. 12, 2020.

(51) Int. Cl.

| | |
|---|---|
| ***A61K 31/4025*** | (2006.01) |
| ***A61K 9/14*** | (2006.01) |
| ***A61K 31/095*** | (2006.01) |
| ***A61K 31/357*** | (2006.01) |
| ***A61K 31/69*** | (2006.01) |
| ***A61K 31/7048*** | (2006.01) |
| ***A61K 47/28*** | (2006.01) |
| ***A61K 47/68*** | (2017.01) |

(52) U.S. Cl.

CPC ............ *A61K 31/4025* (2013.01); *A61K 9/14* (2013.01); *A61K 31/095* (2013.01); *A61K 31/357* (2013.01); *A61K 31/69* (2013.01); *A61K 31/7048* (2013.01); *A61K 47/28* (2013.01); *A61K 47/6809* (2017.08)

(58) Field of Classification Search

None

See application file for complete search history.

(56) References Cited

U.S. PATENT DOCUMENTS

| | | | | |
|---|---|---|---|---|
| 10,792,328 B2 * | 10/2020 | Xu | ....................... | A61K 38/168 |
| 12,133,855 B2 * | 11/2024 | Xu | ....................... | C07D 207/09 |
| 2019/0381189 A1 | 12/2019 | Xu | | |
| 2020/0214982 A1 | 7/2020 | Liu et al. | | |

FOREIGN PATENT DOCUMENTS

| | | |
|---|---|---|
| WO | WO-2014/028487 A1 | 2/2014 |
| WO | WO-2014/134445 A1 | 9/2014 |
| WO | WO-2018/140220 A1 | 8/2018 |
| WO | WO-2019/152848 | 8/2019 |
| WO | WO-2021/252769 A1 | 12/2021 |

OTHER PUBLICATIONS

Flynn et al., “Correlation and Prediction of Mass Transport across Membranes I: Influence of Alkyl Chain Length on Flux-Determining Properties of Barrier and Diffusant,” Journal of Pharmaceutical Sciences, 61(6): 838-852 (1972).

International Search Report and Written Opinion for International Application No. PCT/US2021/036819 dated Sep. 22, 2021.

Li et al., “Combinatorial Library of Cyclic Benzylidene Acetal-Containing pH-Responsive Lipidoid Nanoparticles for Intracellular mRNA Delivery,” Bioconjugate Chemistry, 31: 1835-1843 (2020).

Extended European Search Report for EP Application No. 21823100.9 dated Jun. 24, 2024.

* cited by examiner

*Primary Examiner* — Lauren Wells

(74) *Attorney, Agent, or Firm* — Foley Hoag LLP; Dana M. Gordon; Alexander J. Chatterley

(57) ABSTRACT

Disclosed are lipidoid compounds as well as lipidoid nanoparticles comprising such compounds.

20 Claims, 15 Drawing Sheets

B

R-O16CBA

2x

O16CBA

| Lipidoid | Formula | Cal. $[M+H]^+$ | Obs. $[M+H]^+$ |
|---|---|---|---|
| 75-O16CBA | $C_{52}H_{85}N_2O_{14}$ | 961.60 | 961.64 |
| 76-O16CBA | $C_{52}H_{83}N_2O_{14}$ | 959.58 | 959.73 |
| 77-O16CBA | $C_{53}H_{85}N_2O_{14}$ | 973.60 | 973.73 |
| 78-O16CBA | $C_{50}H_{81}N_2O_{14}$ | 933.57 | 933.64 |
| 80-O16CBA | $C_{51}H_{83}N_2O_{14}$ | 947.58 | 947.64 |
| 81-O16CBA | $C_{53}H_{87}N_2O_{14}$ | 975.62 | 975.73 |
| 82-O16CBA | $C_{53}H_{85}N_2O_{14}$ | 973.60 | 973.73 |
| 93-O16CBA | $C_{52}H_{80}N_3O_{14}$ | 970.56 | 970.64 |
| 113-O16CBA | $C_{74}H_{118}N_3O_{21}$ | 1384.83 | 1384.91 |
| 306-O16CBA | $C_{76}H_{122}N_3O_{21}$ | 1412.86 | 1412.82 |
| 400-O16CBA | $C_{77}H_{124}N_3O_{21}$ | 1426.87 | 1426.91 |

R-O16CBA

R-O16CBA-1 HexDMBA

R-O16CBA-0 2x HexDMBA

HDMBA HexDMBA HexDMBAH O16CBA

PH-RESPONSIVE LIPIDOID NANOPARTICLES FOR INTRACELLULAR MRNA DELIVERY

RELATED APPLICATION

This application is the § 371 National Stage of PCT/US2021/036819, filed Jun. 10, 2021; which claims the benefit of priority to U.S. Provisional Application No. 63/038,451, filed Jun. 12, 2020.

GOVERNMENT SUPPORT

This invention was made with government support under grants DMR1452122 awarded by the National Science Foundation; R01 EB027170-01 awarded by National Institutes of Health; and UG3 TR002636-01 awarded by National Institutes of Health. The government has certain rights in the invention.

BACKGROUND

The combinatorial library strategy has been shown to be effective for the development of cationic lipid-like (lipidoid) nanoparticles (LNPs) for drug delivery. Lipidoid molecules with various hydrophilic amine heads and hydrophobic tails have been synthesized and used to deliver small molecules, proteins and peptides, ribonucleoproteins (RNP), and nucleic acids (mRNA, siRNA, ASO, pDNA etc.), both in vitro and in vivo. Lipidoid molecular design and nanoparticle supramolecular structure optimization strategies have achieved better delivery performances by improving delivery specificity, enhancing efficacy, and reducing side-effects. In order to further refine molecular structure design, we have incorporated functional groups with stimuli-responsive degradable features into combinatorial lipidoid molecules.

A library of reduction-responsive disulfide bond-containing lipidoid nanoparticles that can be degraded in the presence of glutathione (GSH) and other intracellular reducing agents was reported. These lipidoids were used for siRNA and protein delivery. The concept of a stimuli-responsive combinatorial lipidoid library was further expanded from a biochemical trigger to a physical/external trigger. This was achieved through the integration of the o-nitrobenzyl ester group into the lipidoid tail structures. Photo-degradable lipidoid nanoparticles were then fabricated and used for small molecule drug delivery.

Each library of stimuli-responsive lipidoids has its own unique physicochemical properties. Creating and expanding these libraries helps to enrich our molecular toolbox for nano drug delivery applications.

SUMMARY

In certain aspects, provided herein are compounds of formula I:

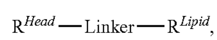

(I)

and pharmaceutically acceptable salts thereof, wherein $R^{Head}$ is

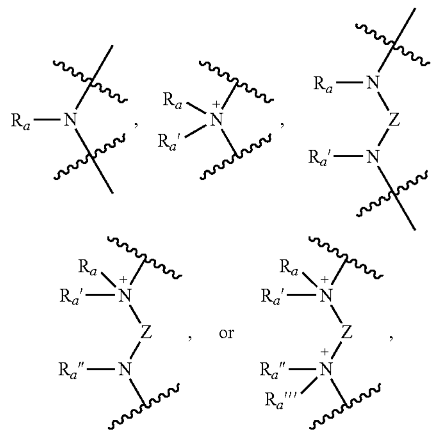

$R^a$, $R^{a'}$, $R^{a''}$, and $R^{a'''}$ independently are $R^{Lipid}$, H, $C_1$-$C_{20}$ alkyl, $C_2$-$C_{20}$ alkenyl, $C_2$-$C_{20}$ alkynyl, $C_3$-$C_{20}$ cycloalkyl, $C_1$-$C_{20}$ heteroalkyl, $C_1$-$C_{20}$ heterocycloalkyl, aryl, or heteroaryl, wherein $R^a$ and $R^{a'}$ or $R^{a''}$ and $R^{a'''}$ are not both $R^{Lipid}$.

Z is a $C_1$-$C_{20}$ bivalent aliphatic radical, a $C_1$-$C_{20}$ bivalent heteroaliphatic radical, a bivalent aryl radical, or a bivalent heteroaryl radical;

Linker is an acid labile moiety that is cleavable under aqueous acidic conditions;

each instance of $R^{Lipid}$ independently is $C_1$-$C_{20}$ alkyl, $C_2$-$C_{20}$ alkenyl, $C_2$-$C_{20}$alkynyl or

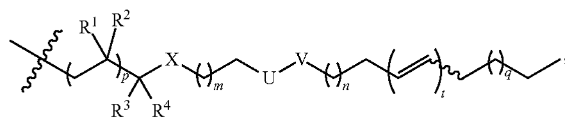

wherein:

$R^1$ and $R^2$ independently are H, OH, $NHR^{30}$, or SH;

$R^3$ and $R^4$ are both H; or $R^3$ and $R^4$ are taken together to form an oxo (=O) group;

X is $CH_2$, O, $NR^{30}$, or S;

$R^{30}$ is H, $C_{1-6}$ alkyl, $C_{1-6}$ alkenyl, or $C_{1-6}$ alkynyl;

U and V independently are S, Se, O, or $CH_2$;

m is an integer selected from 1 to 3;

n is an integer selected from 1 to 14;

p is 0 or 1;

q is an integer selected from 1 to 10; and t is 0, 1, or 2.

In certain aspects, provided are lipidoid nanoparticles, comprising a compound disclosed herein.

BRIEF DESCRIPTION OF THE DRAWINGS

FIG. 2F is a summary of chemical formulas and calculated and observed molecular weights of R-O16CBA lipidoids.

DETAILED DESCRIPTION

Figure 1A:
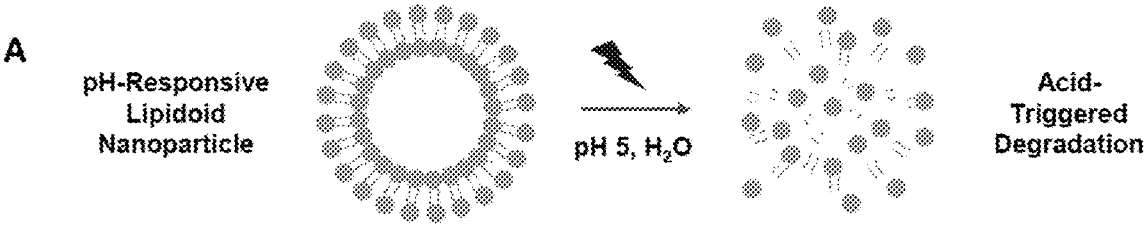
FIG. 1A is a schematic illustration of the acid-triggered degradation of lipidoid nanoparticles.

In certain aspects, provided herein are compounds of formula I:

$$R^{Head}—Linker—R^{Lipid}, \quad (I)$$

and pharmaceutically acceptable salts thereof, wherein $R^{Head}$ is

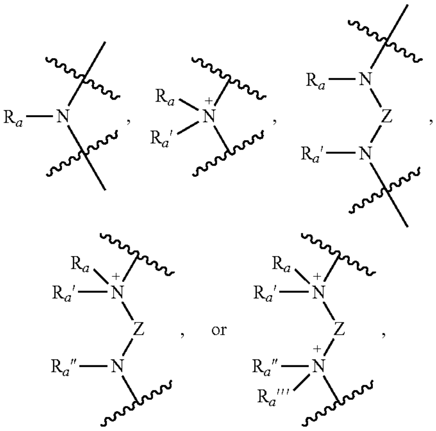

, or , $R^a$, $R^{a'}$, $R^{a''}$, and $R^{a'''}$ independently are $R^{Lipid}$, H, $C_1$-$C_{20}$ alkyl, $C_2$-$C_{20}$ alkenyl, $C_2$-$C_{20}$ alkynyl, $C_3$-$C_{20}$ cycloalkyl, $C_1$-$C_{20}$ heteroalkyl, $C_1$-$C_{20}$ heterocycloalkyl, aryl, or heteroaryl, wherein $R^a$ and $R^{a'}$ or $R^{a''}$ and $R^{a'''}$ are not both $R^{Lipid}$;

Z is a $C_1$-$C_{20}$ bivalent aliphatic radical, a $C_1$-$C_{20}$ bivalent heteroaliphatic radical, a bivalent aryl radical, or a bivalent heteroaryl radical;

Linker is an acid labile moiety that is cleavable under aqueous acidic conditions;

each instance of $R^{Lipid}$ independently is $C_1$-$C_{20}$ alkyl, $C_2$-$C_{20}$ alkenyl, $C_2$-$C_{20}$ alkynyl or

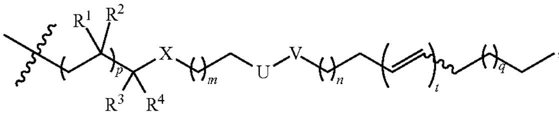

, wherein:

$R^1$ and $R^2$ independently are H, OH, $NHR^{30}$, or SH;

$R^3$ and $R^4$ are both H; or $R^3$ and $R^4$ are taken together to form an oxo (=O) group;

X is $CH_2$, O, $NR^{30}$, or S;

$R^{30}$ is H, $C_{1-6}$ alkyl, $C_{1-6}$ alkenyl, or $C_{1-6}$ alkynyl;

U and V independently are S, Se, O, or $CH_2$;

m is an integer selected from 1 to 3;

n is an integer selected from 1 to 14;

p is 0 or 1;

q is an integer selected from 1 to 10; and t is 0, 1, or 2.

In certain embodiments, $R^{Head}$ is

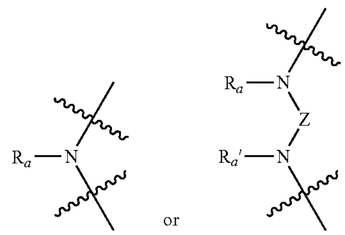

or .

In certain embodiments, $R^a$ and $R^{a'}$ independently are $R^{Lipid}$, H, or $C_1$-$C_{20}$ alkyl.

In certain embodiments, $R^{Head}$ is derived from a compound selected from the group consisting of

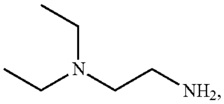

75

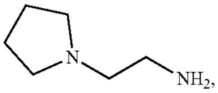

76

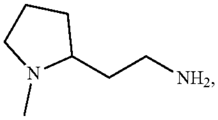

77

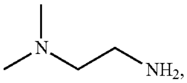

78

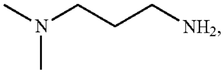

80

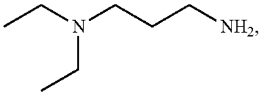

81

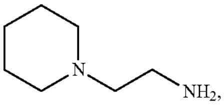

82

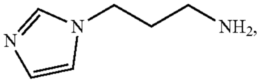

93

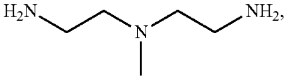

113

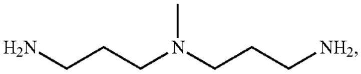

306 and

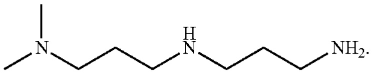

400

In certain embodiments, $R^{Head}$ is derived from a compound selected from the group consisting of

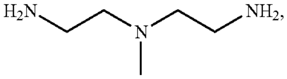

113

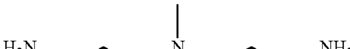

306 and

-continued

400

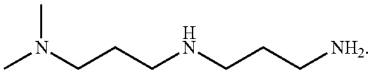

In certain embodiments, each instance of $R^{Lipid}$ independently is $C_1$-$C_{20}$ alkyl, $C_2$-$C_{20}$ alkenyl, or $C_2$-$C_{20}$ alkynyl.

In certain embodiments, each instance of $R^{Lipid}$ independently is

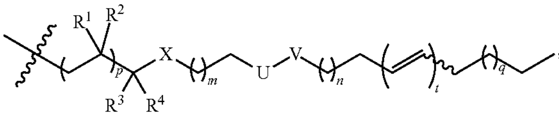

In certain embodiments, $R^1$ and $R^2$ are H. In certain embodiments, $R^1$ is H; and $R^2$ is OH.

In certain embodiments, $R^3$ and $R^4$ are H. In certain embodiments, $R^3$ and $R^4$ taken together form an oxo (=O) group.

In certain embodiments, Z is $CH_2$, O, or $NR^{30}$. In certain embodiments, Z is $CH_2$. In certain embodiments, Z is O. In certain embodiments, Z is $NR^{30}$.

In certain embodiments, U and V are independently —$CH_2$— or —O—. In certain embodiments, U and V are independently —$CH_2$— or —O—, wherein U and V are not the same. In certain embodiments, U and V are independently —$CH_2$— or —S—. In certain embodiments, U and V are both —$CH_2$—. In certain embodiments, U and V are both —S—.

In certain embodiments, m is 1 or 2.

In certain embodiments, n is an integer selected from 4-12. In certain embodiments, n is an integer selected from 6-10.

In certain embodiments, p is 0. In certain embodiments, p is 1.

In certain embodiments, q is an integer selected from 2-8. In certain embodiments, q is an integer selected from 4-8.

In certain embodiments, t is 0. In certain embodiments, t is 1.

In certain embodiments, Linker is represented by formula II:

(II)

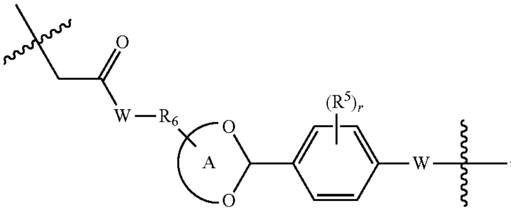

wherein:

W is O or NH;

each of $R^5$ independently is hydrogen, halogen, nitro, cyano, amino, hydroxyl, alkoxy, alkylthio, alkyl, alkenyl, alkynyl, aralkyl, heteroaralkyl, carbocyclyl, heterocyclyl, aryl, or heteroaryl;

r is an integer selected from 0 to 4;

A is a 5- to 8-membered heterocycle; and $R^6$ is absent; or $R^6$ is alkylene or alkenylene;

In certain embodiments, W is O. In certain embodiments, W is NH.

In certain embodiments, $R^5$ is alkoxy, e.g., methoxy.

In certain embodiments, r is 2.

In certain embodiments, $R^6$ is absent. In certain embodiments, $R^6$ is methylene.

In certain embodiments, A is a 6-membered heterocycle.

In certain embodiments, A is unsubstituted.

In certain embodiments, A is substituted with halogen, nitro, cyano, amino, hydroxyl, alkoxy, alkylthio, alkyl, alkenyl, alkynyl, aralkyl, heteroaralkyl, carbocyclyl, heterocyclyl, aryl, or heteroaryl.

In certain embodiments, each instance of $R^{Lipid}$ independently is selected from the group consisting of n-pentyl, n-hexyl, n-heptyl, n-octyl,

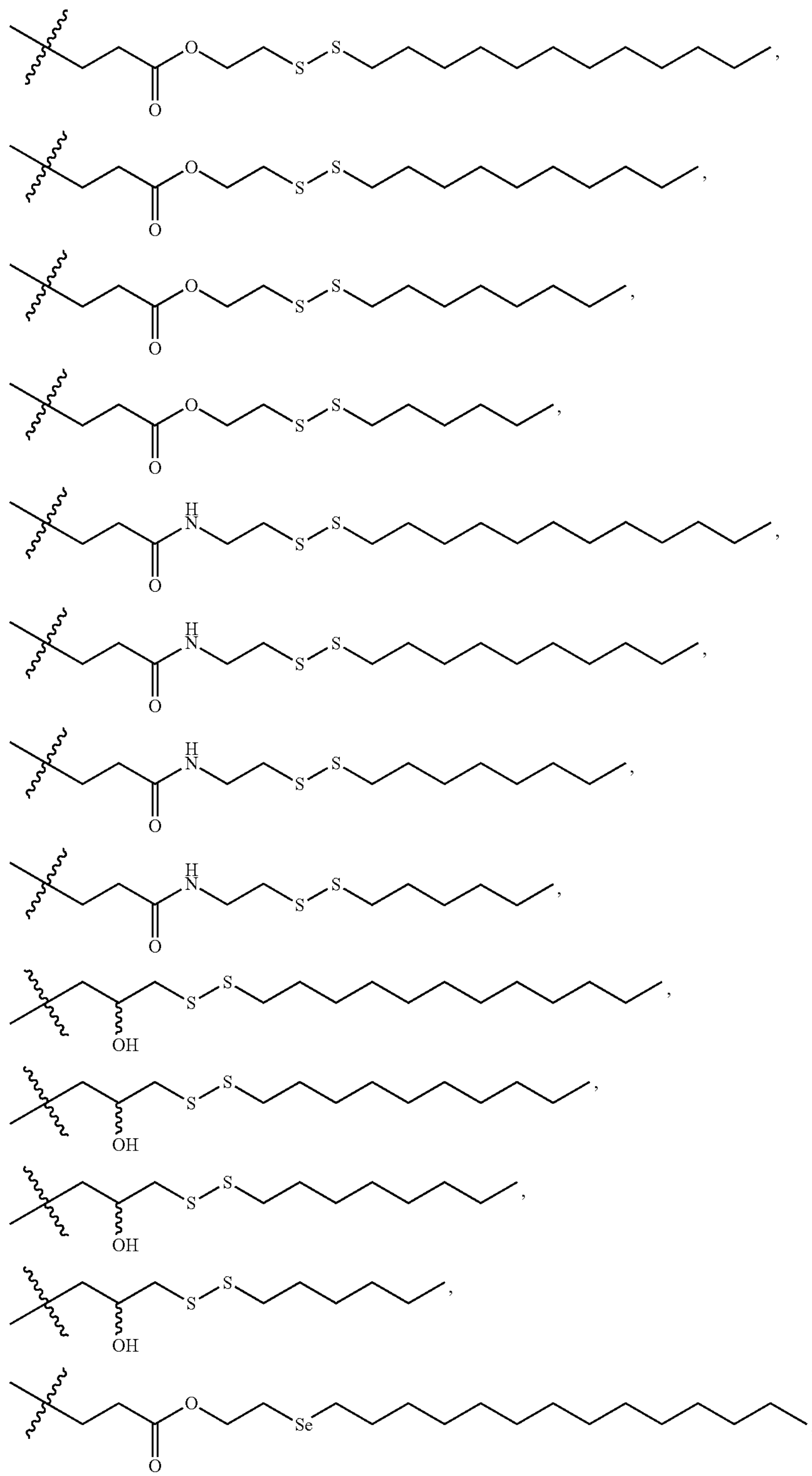

-continued
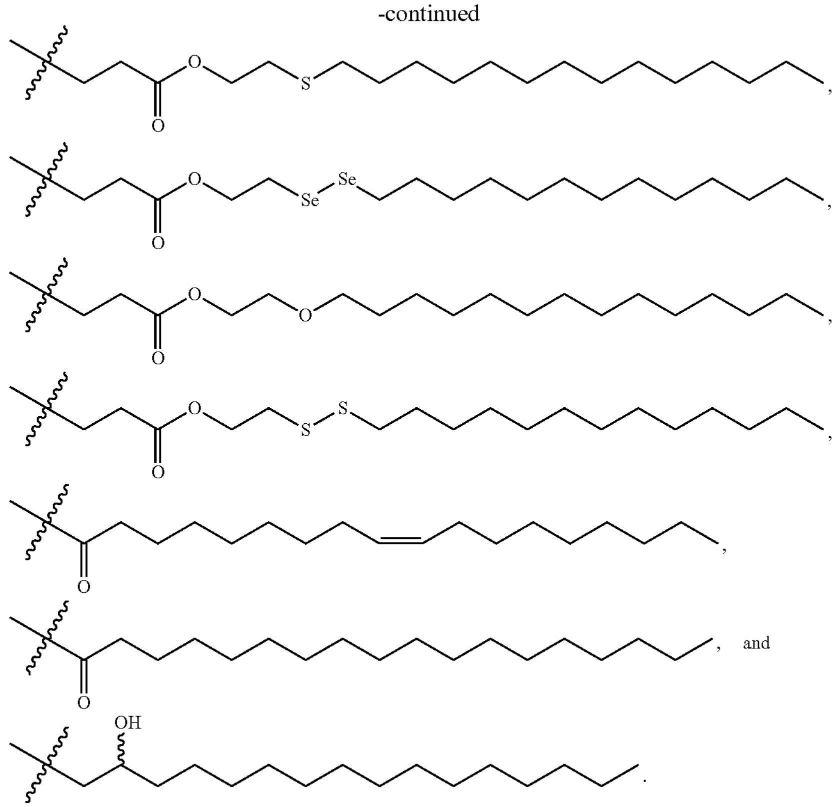
and
In certain embodiments, the compound is a compound of formula III:
(III)
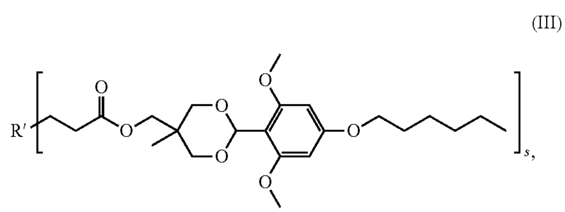
wherein
R' is derived from a compound selected from the group consisting of
75
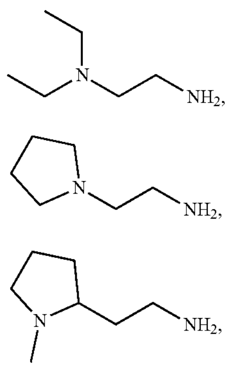
76
77
-continued
78
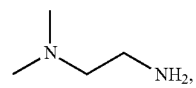
80
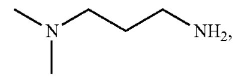
81
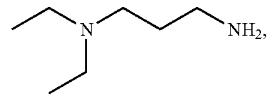
82
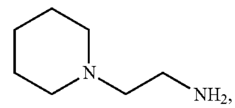
93
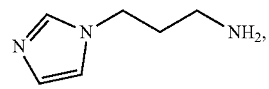
113
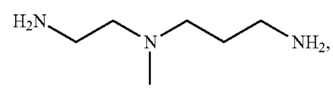
306
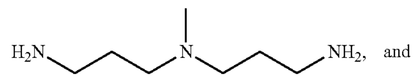
and -continued

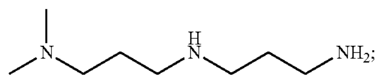

and s is an integer selected from 1 to 4, as valency permits.

In certain aspects, provided are lipidoid nanoparticles, comprising a compound disclosed herein.

In certain embodiments, the lipidoid nanoparticle further comprises cholesterol.

In certain embodiments, the weight ratio of the compound to the cholesterol is about 2:1 to about 8:1.

In certain embodiments, the weight ratio of the compound to the cholesterol is about 4:1.

In certain embodiments, the lipidoid nanoparticle further comprises DOPE, DSPC, DOPC; or DMG-PEG2K; wherein DSPC has the structure:

In certain embodiments, the lipidoid nanoparticle further comprises DOPE.

In certain embodiments, the weight ratio of the compound to the DOPE is about 4:1 to about 1:1. In certain embodiments, the weight ratio of the compound to the DOPE is about 4:1 or about 1:1.

In certain embodiments, the lipidoid nanoparticle disclosed herein further comprises an mRNA. In certain embodiments, the mRNA is green fluorescence protein (GFP) mRNA.

In certain embodiments, further comprising a small molecule. In certain embodiments, the small molecule is an antifungal agent or a chemotherapeutic agent. In certain embodiments, the small molecule is selected from the group consisting of bortezomib, imatinib, gefitinib, erlotinib, afatinib, osimertinib, dacomitinib, daunorubicin hydrochloride, cytarabine, fluorouracil, irinotecan hydrochloride, vincristine sulfate, methotrexate, paclitaxel, vincristine sulfate, epirubicin, docetaxel, cyclophosphamide, carboplatin,

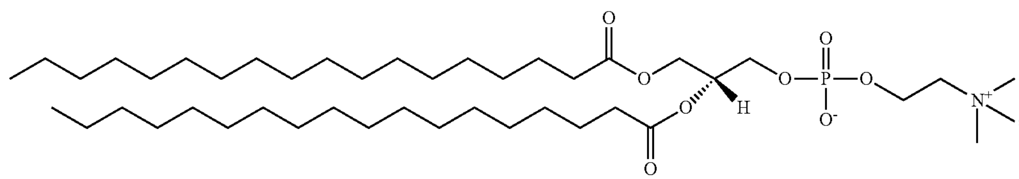 [SMILES: CCCCCCCCCCCCCCCCCC(=O)OC[C@H](COP(=O)([O-])OCC[N+](C)(C)C)OC(=O)CCCCCCCCCCCCCCCCC]

DOPE has the structure:

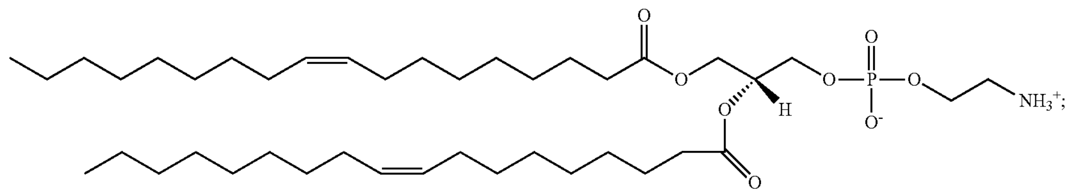

DOPC has the structure:

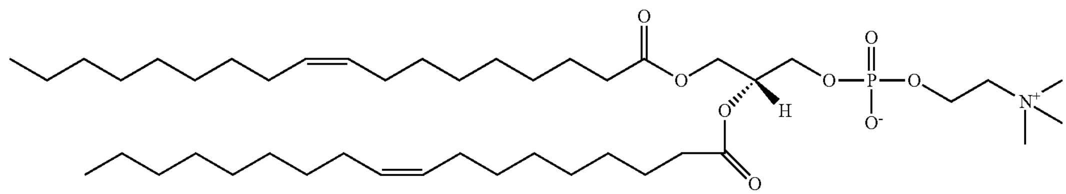

DMG-PEG2K has the structure:

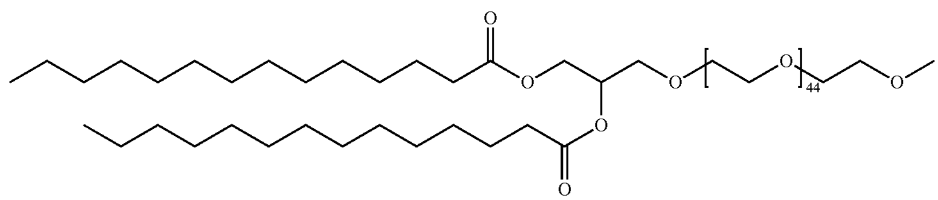

lenalidomide, ibrutinib, abiraterone acetate, enzalutamide, pemetrexed, palbociclib, nilotinib, everolimus, ruxolitinib, epirubicin, pirirubicin, idarubicin, valrubicin, amrubicin, bleomycin, phleomycin, dactinomycin, mithramycin, streptozotecin, pentostatin, mitosanes mitomycin C, enediynes calicheamycin, glycosides rebeccamycin, macrolide lactones epotihilones, ixabepilone, pentostatin, salinosporamide A, vinblastine, vincristine, etoposide, teniposide, vinorelbine, docetaxel, camptothecin, hycamtin, pederin, theopederins, annamides, trabectedin, aplidine, and ecteinascidin 743 (ET743).

In certain embodiments, the small molecule is Amphotericin B or Doxorubicin.

In certain embodiments, the lipidoid nanoparticle has a particle size of about 25 nm to about 1000 nm. In certain embodiments, the lipidoid nanoparticle has a particle size of about 50 nm to about 750 nm. In certain embodiments, the lipidoid nanoparticle has a particle size of about 200 nm to about 500 nm.

In another aspect, provided herein are pharmaceutical compositions, comprising a lipidoid nanoparticle disclosed herein, and one or more pharmaceutically acceptable carriers or excipients.

EXAMPLES

In order that the invention described herein may be more fully understood, the following examples are set forth. The examples described in this application are offered to illustrate the compounds, compositions, materials, device, and methods provided herein and are not to be construed in any way as limiting their scope.

Materials and Methods

Materials and Instruments.

All chemicals and solvents used for lipidoid synthesis were purchased from Millipore-Sigma and used without purification unless otherwise noted. $^1$H and $^{13}$C NMR spectra were collected on a Bruker AVIII 500 MHz NMR spectrometer. ESI-MS spectra were collected on a Finnigan LTQ Mass Spectrometer using methanol as a solvent (0.5% acetic acid; v/v). Hydrodynamic sizes of nanoparticles were measured by a Brookhaven Zeta-PALS particle size analyzer. TEM images were taken on a FEI Technai Transmission Electron Microscope. GFP mRNA transfected cells were analyzed with an Invitrogen Attune NxT Flow Cytometer, and data was analyzed using FlowJo software.

Synthesis of O16CBA.

Figure 7:
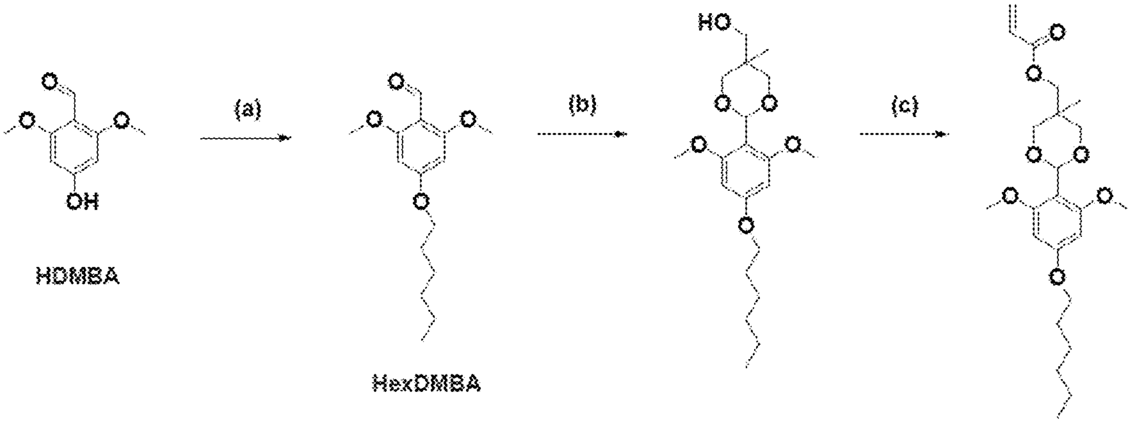
FIG. 7 shows a synthetic route employed for the preparation of acid-degradable hydrophobic tail, O16CBA.
Figure 8:
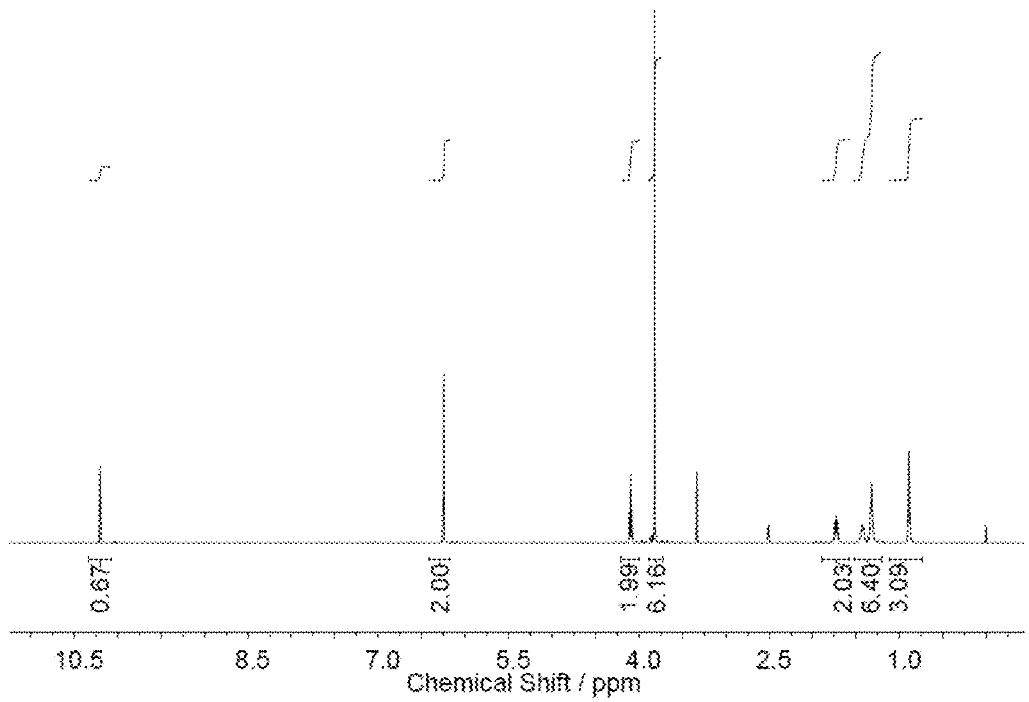
FIG. 8 is a $^1$H NMR spectrum of HexDMBA in DMSO-d6.

The synthetic route for cyclic benzylidene acetal-containing hydrophobic tail, O16CBA, is shown in FIG. 7. 4-hydroxy-2,6-dimethoxybenzaldehyde (HDMBA; 5.1 g, 28.0 mmol) was dissolved in acetone (100 mL). Potassium carbonate (4.6 g, 33.3 mmol) was added followed by 1-bromohexane (6.8 g, 41.2 mmol) with continuous stirring. The reaction was maintained at 55° C. for 24 h. The mixture was cooled to room temperature and filtered with filter paper. The solvent was then removed through rotary evaporation, and the product was purified by silica gel column chromatography, with hexane and ethyl acetate as the mobile phase. HexDMBA was obtained as a white solid (5.2 g; yield ~70%) and structure was confirmed by 1H NMR (FIG. 8).

Figure 9:
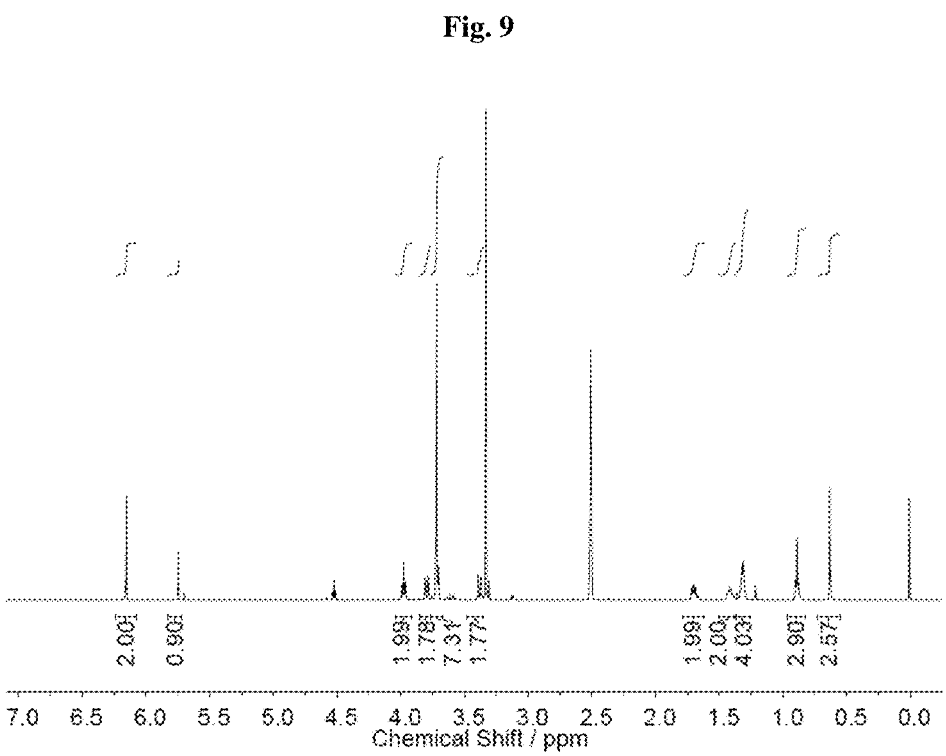
FIG. 9 is a $^1$H NMR spectrum of HexDMBAH in DMSO-d6.

HexDMBAH was synthesized using a similar procedure reported previously. Briefly, HexDMBA (5.2 g, 19.5 mmol) and 1,1,1-tris(hydroxymethyl)ethane (6.7 g, 55.9 mmol) were dissolved in anhydrous tetrahydrofuran (200 mL). 5 Å molecular sieves (30 g) and p-toluenesulfonic acid (0.44 g, 2.56 mmol) were then added. The reaction mixture was stirred at room temperature for 12 h, molecular sieves were filtered out, and solvent was removed via rotary evaporation. HexDMBAH was purified by silica gel column chromatography, with hexane and ethyl acetate as the mobile phase. HexDMBAH was recovered as a white solid (5.4 g; yield ~75%), and its structure was confirmed by 1H NMR (FIG. 9).

Figure 2A:
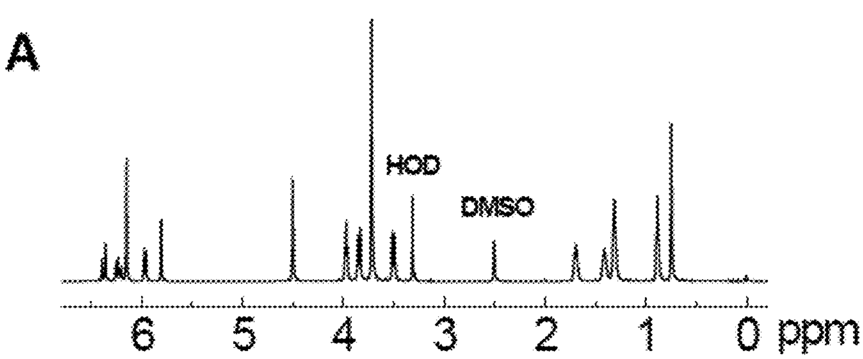
FIG. 2A is a $^1$H NMR spectrum of O16CBA tail.
Figure 2B:
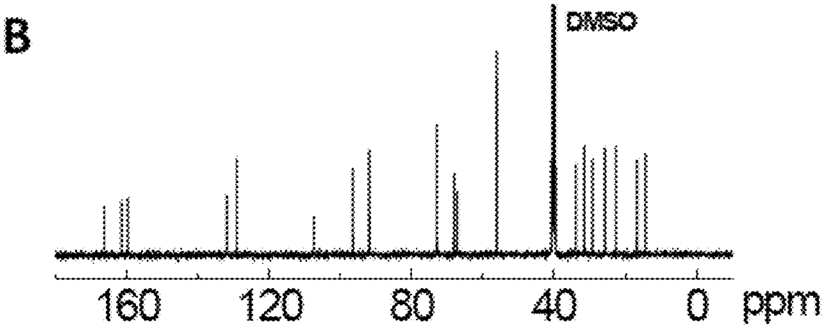
FIG. 2B is a $^{13}$C NMR spectrum of O16CBA tail.

HexDMBAH (5.4 g, 14.7 mmol) was dissolved in dichloromethane (~150 mL) followed by triethylamine (2.2 g, 22.1 mmol). The solution was cooled in an ice bath for 15 minutes, and acryloyl chloride (2.00 g, 22.1 mmol) was slowly added dropwise. The reaction mixture was allowed to warm to room temperature and was stirred for 12 h. After silica gel column chromatography purification, with the same mobile phase as previously described, O16CBA was obtained as a white solid (4.5 g; yield ~73%). Its structure was confirmed using $^1$H and $^{13}$C NMR (FIGS. 2A and 2B).

Synthesis of O16CBA-Tailed Lipidoids.

Figure 2C:
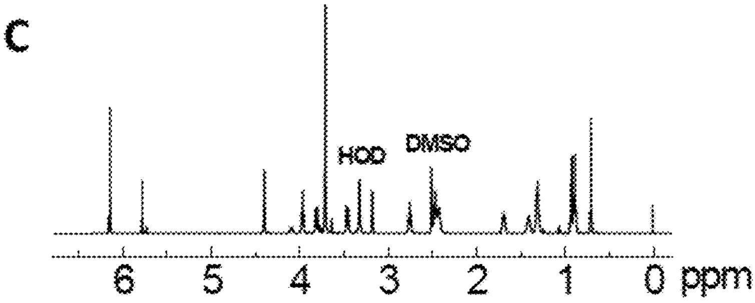
FIG. 2C is a $^1$H NMR spectra of 75-O16CBA lipidoid.
Figure 2D:
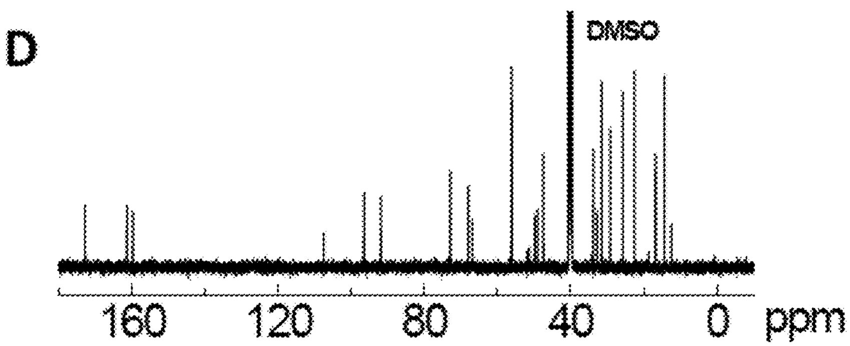
FIG. 2D is a $^{13}$C NMR spectra of 75-O16CBA lipidoid.
Figure 2E:
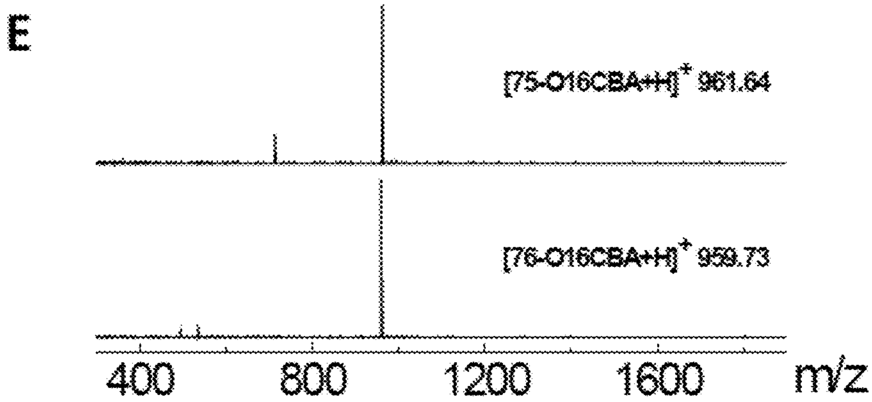
FIG. 2E is a set of ESI-MS spectra of 75-O16CBA and 76-O16CBA.
Figure 10:
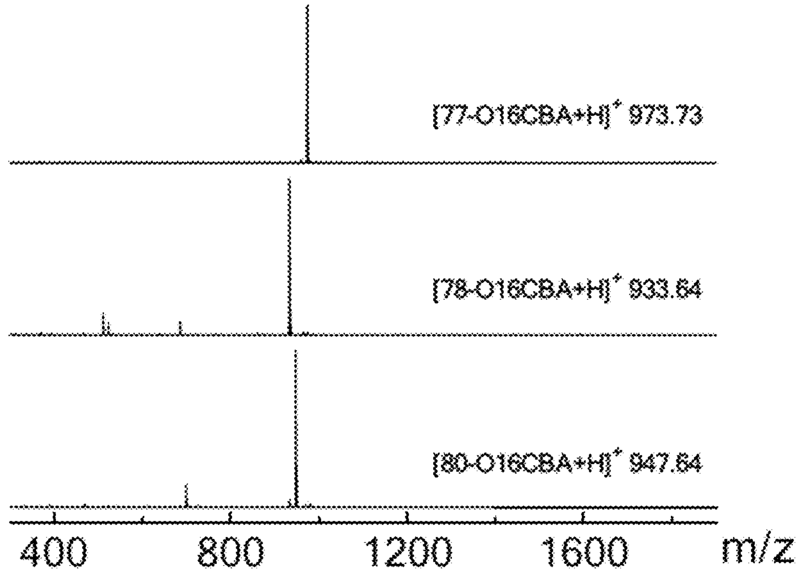
FIG. 10 is a set of ESI-MS spectra of cyclic benzylidene acetal-containing lipidoids, 77-O16CBA, 78-O16CBA, and 80-O16CBA.

Lipidoids were synthesized from the O16CBA tail and amine heads via the Michael addition reaction, using our previously reported procedure. To synthesize 75-O16CBA etc., amines (75, 76, 77, 78, 80, 81, 82, and 93) were mixed with O16CBA at a 1/2.2 molar ratio. To synthesize 113-O16CBA etc., amines (113, 306, and 400) were mixed with O16CBA at a 1/3.3 molar ratio. These mixtures were placed in Teflon-lined glass screw-top vials for 48 h at 70° C. with continuous stirring. The mixtures were cooled to room temperature and diluted with dichloromethane. The crude products were purified using a Teledyne ISCO Chromatography purification system, with dichloromethane and methanol as the mobile phase. The lipidoids were characterized by $^1$H NMR, $^{13}$C NMR (FIGS. 2C and D), and ESI-MS (FIGS. 2E and 10).

Fabrication of Lipidoid Nanoparticles.

The lipidoid nanoparticles without helper lipids (i.e. cholesterol and DOPE) were prepared by dissolving pure O16CBA lipidoids (75-O16CBA etc.) in ethanol. Water was added as the selective solvent to trigger the self-assembly process with 10 min of sonication in an ultrasonic water bath. This was followed by dialysis (MWCO 3.5 kDa; Slide-A-Lyzer dialysis cassette; ThermoFisher Scientific) to remove the ethanol. The lipidoid nanoparticles with cholesterol and DOPE were prepared by dissolving a precalculated amount of O16CBA lipidoids, cholesterol, and DOPE (O16CBA lipidoid/cholesterol/DOPE=4/1/1 or 4/1/4; weight ratio) in ethanol and then water. This was again followed by sonication and dialysis.

GFP mRNA—(purchased from TriLink) loaded lipidoid nanoparticles were fabricated by mixing lipidoid nanoparticles (with or without helper lipids) and mRNA in PBS with a weight ratio of 10/1 (O16CBA lipidoid/mRNA). The mixture was incubated at room temperature for 15 min before use.

Intracellular Delivery of mRNA.

48-well plates were seeded with HeLa cells at an initial concentration of 20 k cells per well dispersed in 250 μL of DMEM cell culture media and incubated for 24 h. 20 μL of the mRNA-loaded lipidoid nanoparticles were then added into each well. The cells were incubated for another 24 h at 37° C. and 5% $CO_2$ prior to flow cytometry analysis.

MT Assay.

96-well plates were seeded with HeLa cells at an initial concentration of 5000 cells per well dispersed in 100 μL of DMEM cell culture media and incubated for 24 h. Lipidoid nanoparticles were then added into each well. The cells were incubated for another 24 h at 37° C. and 5% CO2 before MTT reagent (5 mg/mL; in 30 μL PBS) was added. After 4 h incubation, the culture medium was carefully removed and 200 μL of DMSO was added to each well. After dissolving the formazan with DMSO solution, the absorbance at 570 nm was determined using a microplate reader (Molecular Devices Spectra Max).

Statistical Analysis.

Data were reported as mean±SD. Experiments were repeated at least three times. Student's t-tests were performed to determine the significance of differences between groups. P values less than 0.05 were considered to be statistically significant.

Example 1. Lipoid Synthesis

The pH-responsive cyclic benzylidene acetal-containing hydrophobic tail, O16CBA, was first synthesized through a multistep reaction (FIG. 7). Chemical structures of O16CBA (FIGS. 2A and 2B) and its precursors (FIGS. 8 and 9) were confirmed by NMR analysis.

Figure 1B:
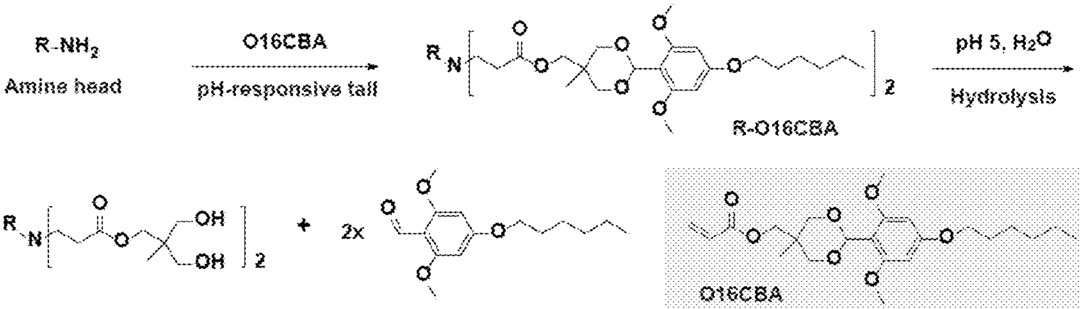
FIG. 1B is the synthetic route and an acidic pH-triggered hydrolysis reaction for R-O16CBA lipidoids.
Figure 1C:
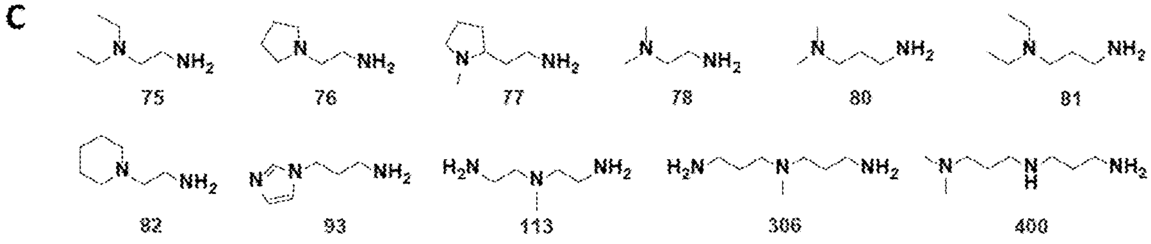
FIG. 1C shows the chemical structures of exemplary amine head groups.

A combinatorial library of cationic lipidoids was then synthesized through the Michael addition reaction by reacting acrylate-containing O16CBA tails with commercially available amine-containing head groups (75, 76, 77 etc.; FIGS. 1B and 1C). Lipidoids were nomenclated as R-O16CBA (where R represents the amine number) and chemical structures were confirmed by NMR (FIGS. 2C and 2D) and ESI-MS spectra (FIGS. 2E and 10). The summarized MS data (FIG. 2F) showed that the calculated and observed molecular weights of the O16CBA lipidoid library were consistent, indicating that the O16CBA-based lipidoids were successfully synthesized. It should be noted that analogs of O16CBA can be synthesized through the same method by using different benzaldehyde derivatives and haloalkanes as reactants (FIG. 7). This can be useful for introducing new functional groups or further optimizing the delivery performances of lipidoid nanoparticles as nanocarriers.

The cyclic benzylidene acetal moiety in the lipidoid tail can be cleaved through a hydrolysis reaction facilitated by acid. It has been previously reported that 2,4,6-trimethoxyphenyl groups containing cyclic acetal groups can be readily degraded at pH 5.23, The R-O16CBA lipidoids synthesized in this study were thus expected to degrade in mild acidic conditions, dissociating the self-assembled nanoparticles (FIGS. 1A and 1B).

Example 2. PH-Responsiveness of R-O16CBA Lipidoids

Figure 3A:
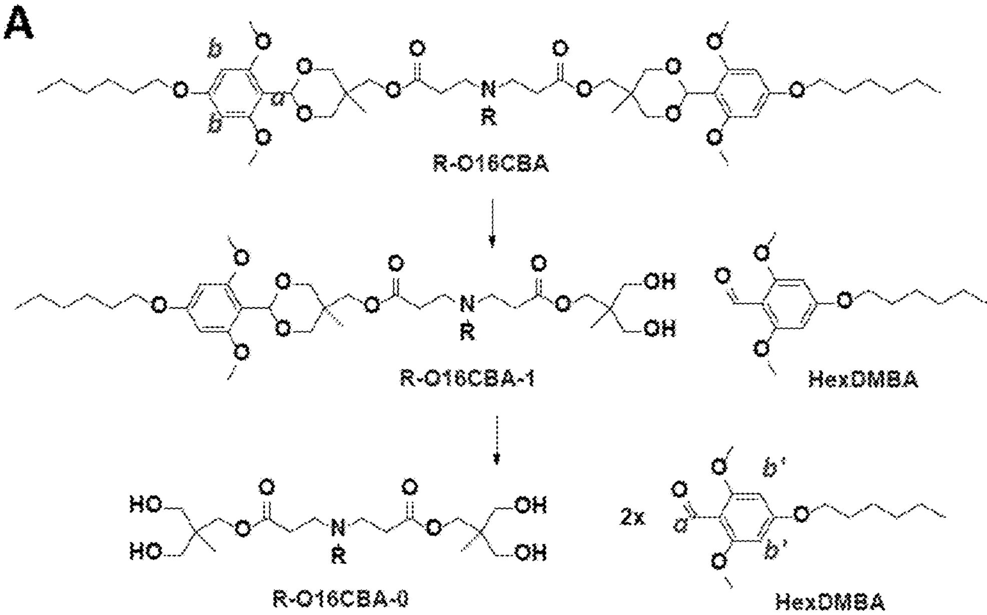
FIG. 3A is a schematic illustration of an acid-induced hydrolysis reaction and tail cleavage of O16CBA lipidoids.
Figure 3B:
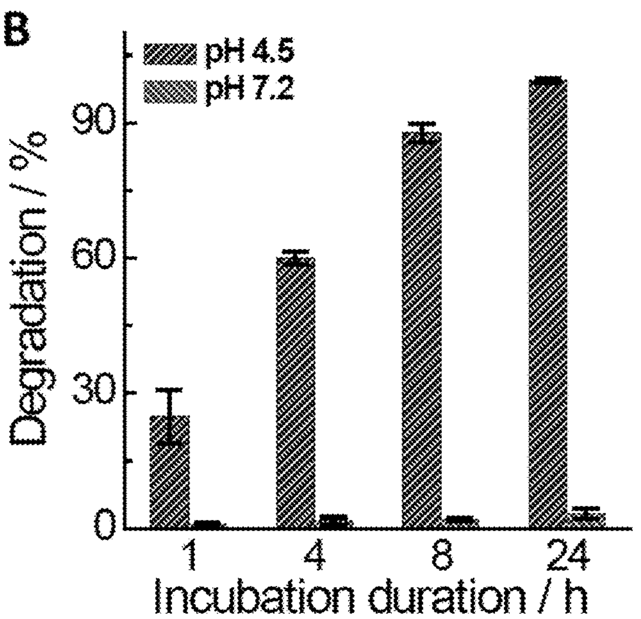
FIG. 3B is a bar graph showing degradation efficacy of the cyclic benzylidene acetal group in 75-O16CBA lipidoids at pH 4.5 and 7.0 for different incubation durations.

In this library, lipidoids containing two tails, such as 75-O16CBA and 76-O16CBA, have both their tails cleaved through acid degradation. During this process, the products R-O16CBA-1, R-O16CBA-0, and HexDMBA can form (FIG. 3A). Lipidoids containing more than two tails (113-, 306-, and 400-O16CBA) can also form more products after degradation. Using characteristic peaks shown in the $^{1}H$ NMR spectrum of the cyclic benzylidene acetal/aldehyde moiety on intact lipidoids and degradation products, the acid-triggered lipidoid degradation process could be studied in real time. Following a previously established procedure, the hydrolysis reactions of 75-O16CBA lipidoids were examined at 37° C. and pH 7.2 or 4.5. As shown in FIG. 3B, the degradation of cyclic benzylidene acetal groups was determined to be 25%, 60%, 88%, and 99% after 1, 4, 8, and 24 h of incubation at a pH of 4.5. The result indicates that most of the tail groups in 75-O16CBA lipidoids were cleaved after 8 h of treatment and almost all were degraded after 24 h. This is consistent with previous reports outlining how 2,4,6-trimethoxyphenyl-containing cyclic acetal groups are highly degradable under acidic conditions.

Figure 3C:
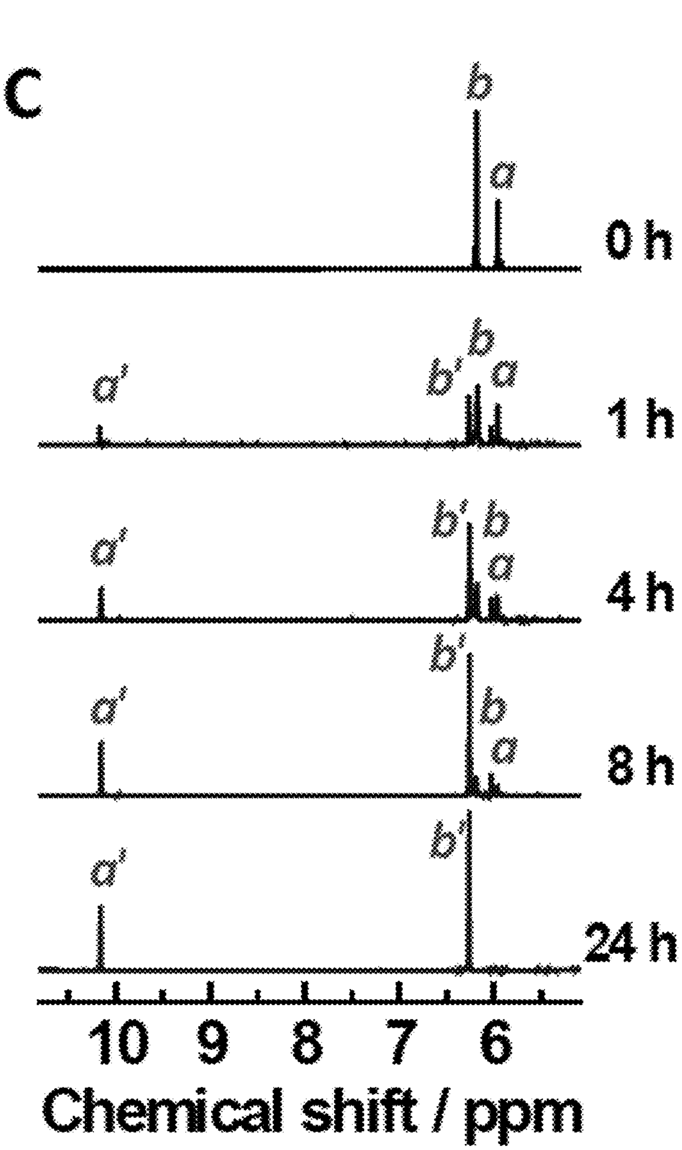
FIG. 3C is a time series of $^1$H NMR spectra of 75-O16CBA lipidoids under pH 4.5.

In comparison, only 1.9% and 3.3% acetal bond degradation occurred for 75-O16CBA lipidoids after 8 and 24 h incubated at pH 7.2. The characteristic proton signals indicated in FIG. 3A can be observed in the 1H NMR spectra of 75-O16CBA at pH 4.5 (FIG. 3C). No peak shift (protons on substituted phenyl group) or new peak generation (proton on aldehyde group) was observed in the spectra of lipidoids in pH 7.2 solution (FIG. 3D) at various incubation time intervals (0, 1, 4, 8, and 24 h).

Figure 3D:
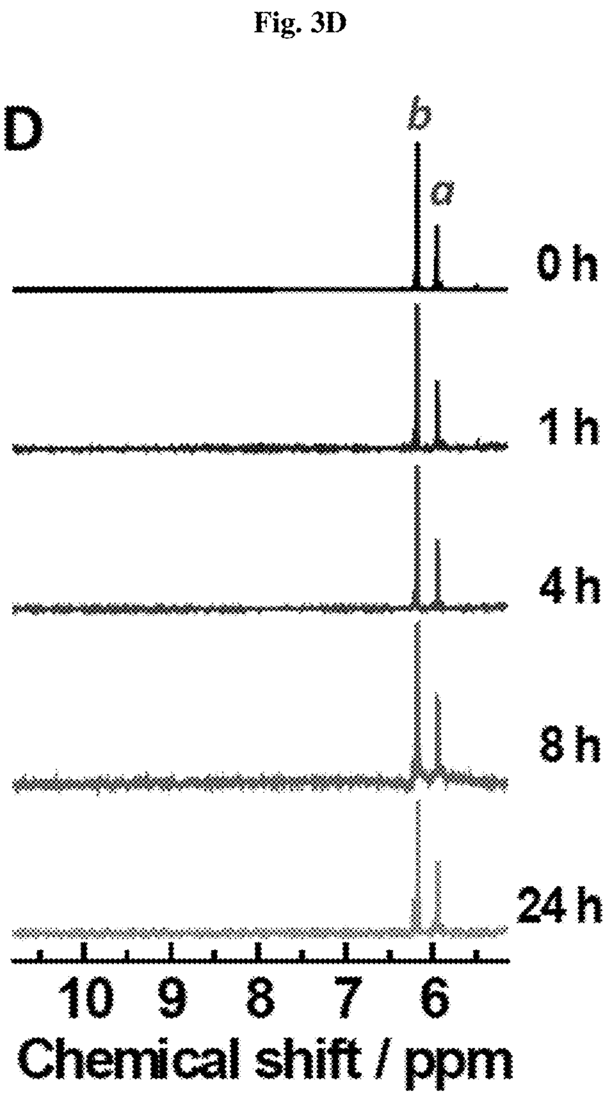
FIG. 3D is a time series of $^1$H NMR spectra of 75-O16CBA lipidoids under pH 7.2.
Figure 3E:
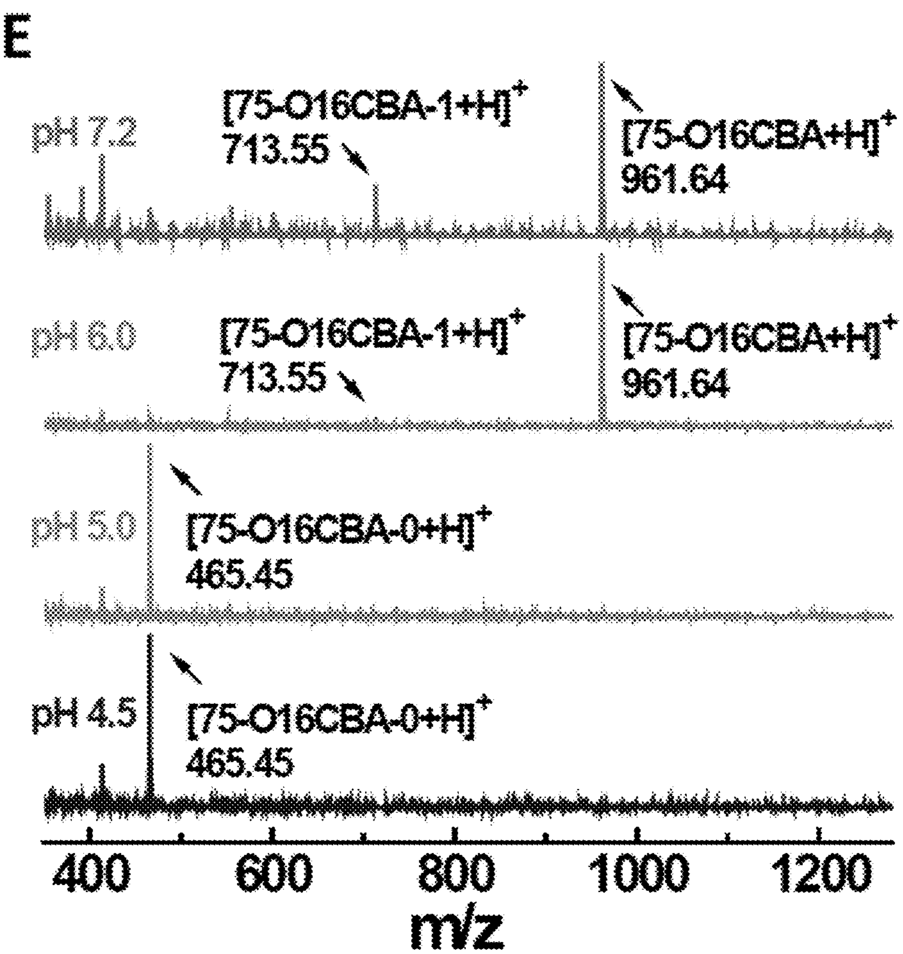
FIG. 3E is an ESI-MS spectra of 75-O16CBA LNPs 24 h after incubation at pH 7.2, 6.0, 5.0, and 4.5.
Figure 11:
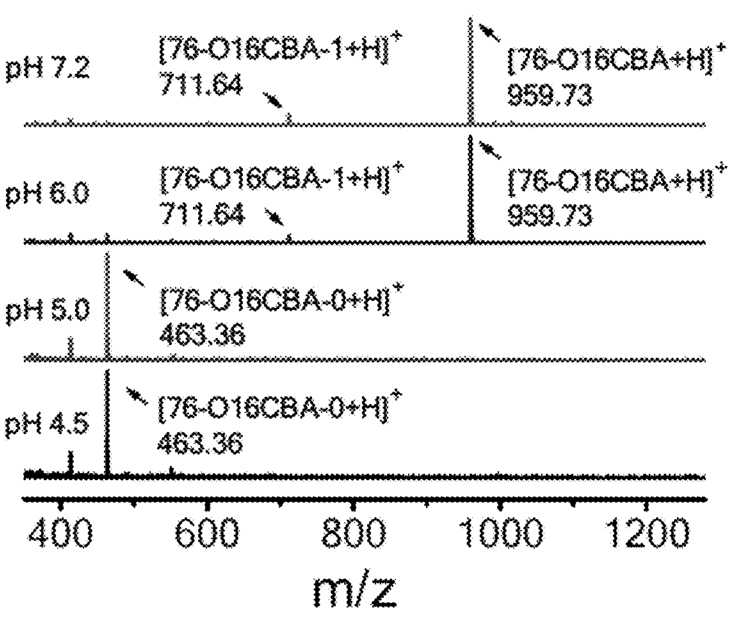
FIG. 11 is a set of ESI-MS spectra of 76-O16CBA LNPs incubated under pH 7.2, 6.0, 5.0, and 4.5 after 24 h.
Figure 12:
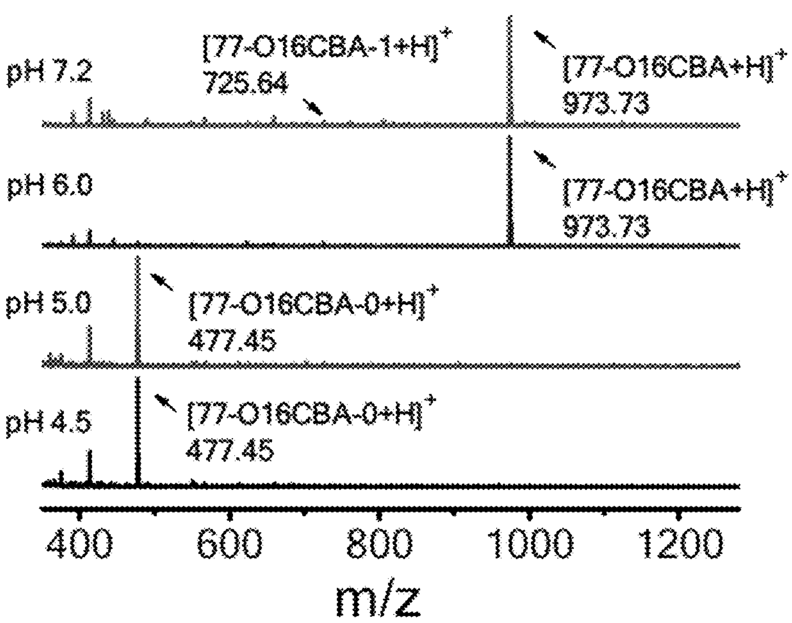
FIG. 12 is a set of ESI-MS spectra of 77-O16CBA LNPs incubated under pH 7.2, 6.0, 5.0, and 4.5 after 24 h.

The acid-triggered lipidoid degradation was further confirmed by ESI-MS. 75-O16CBA, 76-O16CBA, and 77-O16CBA lipidoid nanoparticles were prepared and incubated at 37° C. in aqueous solutions with pH values of 7.2, 6.0, 5.0, and 4.5 respectively. After 24 h, the LNP aqueous solutions were diluted with methanol containing 0.5% acetic acid and examined by ESI-MS. As shown in FIG. 3E, a peak representing intact 75-O16CBA ([M+H]+; m/z 961.64) and a small peak representing 75-O16CBA-1 (m/z 713.55) were observed in the solutions of pH 7.2. It should be noted that the presence of 75-O16CBA-1 in the pH 7.2 solution was most likely due to the degradation induced by acid from the MS test, as the $^{1}H$ NMR did not show the generation of 75-O16CBA-1 or aldehyde byproducts after 24 h of incubation at pH 7.2 (FIG. 3D). The ESI-MS of 75-O16CBA incubated at pH 6.0 showed similar results as that of pH 7.2 since both the intact 75-O16CBA and a small peak of 75-O16CBA-1 were observed. Under pH 4.5, the product 75-O16CBA-0 was detected and no 75-O16CBA-1 or intact 75-O16CBA were observed. This indicates that the degradation of 75-O16CBA was nearly complete after 24 h at pH 4.5, which is consistent with the 1H NMR measurement (FIG. 3B). Samples treated with pH 5.0 conditions revealed very similar results as those at pH 4.5. Furthermore, as shown in FIGS. 11 and 12, the same patterns were observed for two other lipidoids (76-O16CBA and 77-O16CBA).

Example 2. Acid-Induced Degradation of O16CBA Lipidoid Nanoparticles

The morphological change of O16CBA LNPs under acid-induced degradation was studied using TEM and DLS. In this study, 75-O16CBA LNPs were fabricated using a self-assembly procedure. Through TEM examination, it was confirmed that spherical nanoparticles with average sizes of 315 nm formed in the pH 7.2 solution (FIG. 4A).

Due to the self-assembly packing parameters of the lipidoid molecules and the self-assembly procedures that were employed, almost all of our previously studied combinatorial lipidoid nanoparticles have the vesicular/liposomal structures. The supramolecular structures of lipidoid nanoparticles (e.g. morphology, size, etc.) are supposed to be reliant on both of the chemical structures of lipidoid molecules and assembly conditions. The size and distribution of lipidoid nanoparticles can also be further optimized using microfluidics, mechanical extrusion, and other techniques.

Figure 4A:
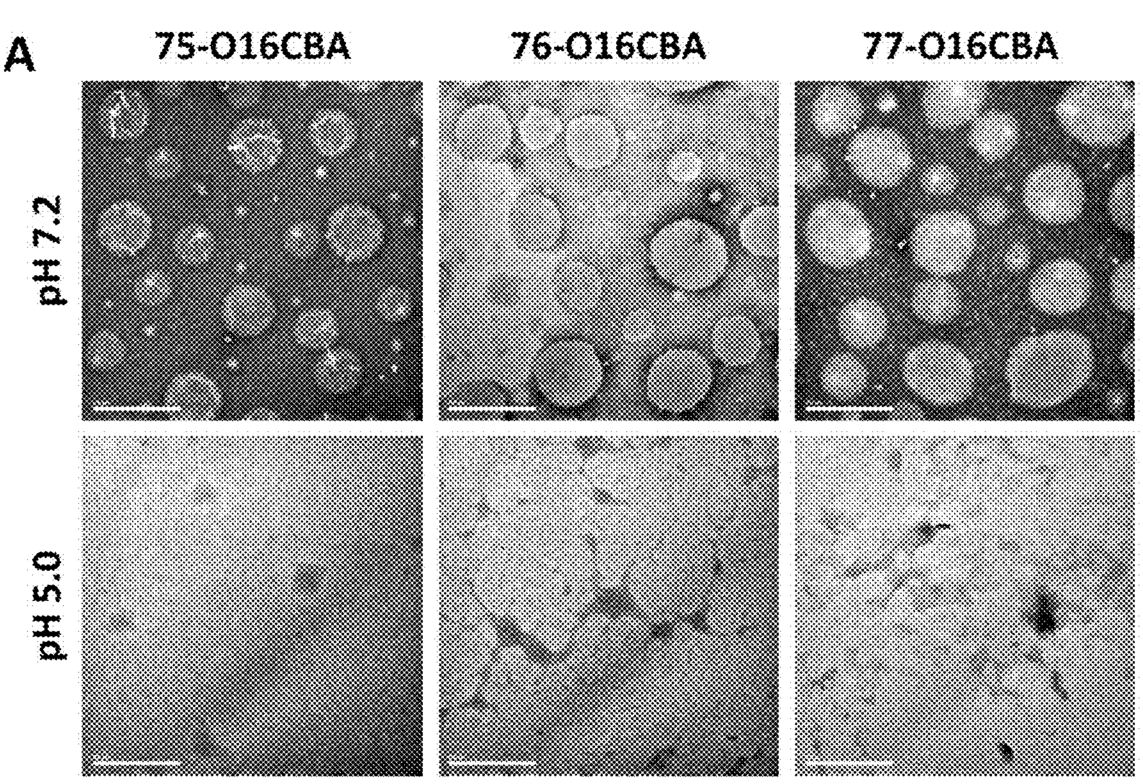
FIG. 4A are a set of TEM images (scale bar=500 nm) of R-O16CBA LNPs in neutral (pH 7.2) and acidic (pH 5.0) solutions.
Figure 4B:
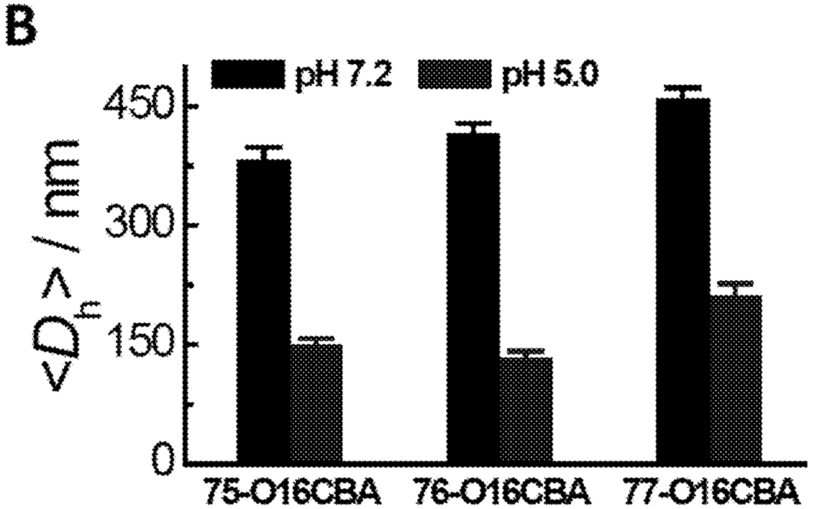
FIG. 4B are the average hydrodynamic diameters of R-O16CBA LNPs in neutral (pH 7.2) and acidic (pH 5.0) solutions.
Figure 4C:
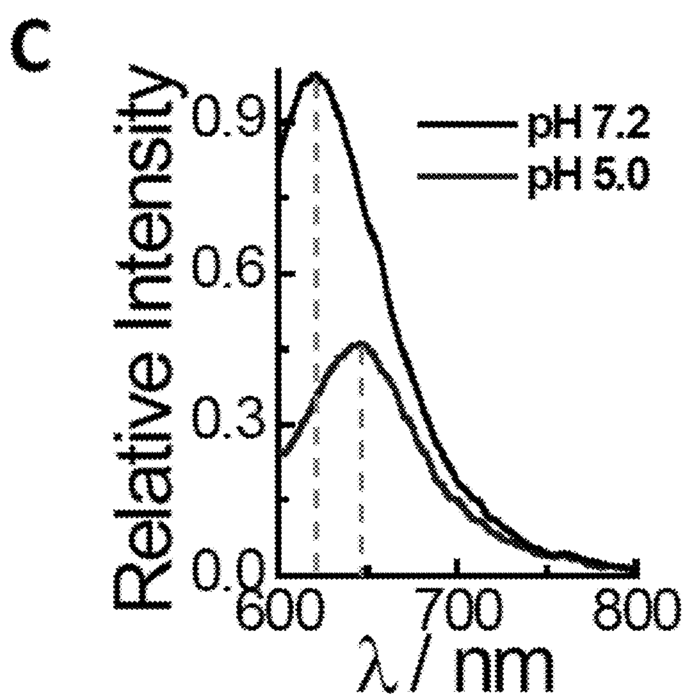
FIG. 4C is a fluorescence emission spectra of NR/75-O16CBA LNPs in pH 7.2 and 5.0 solutions.
Figure 13:
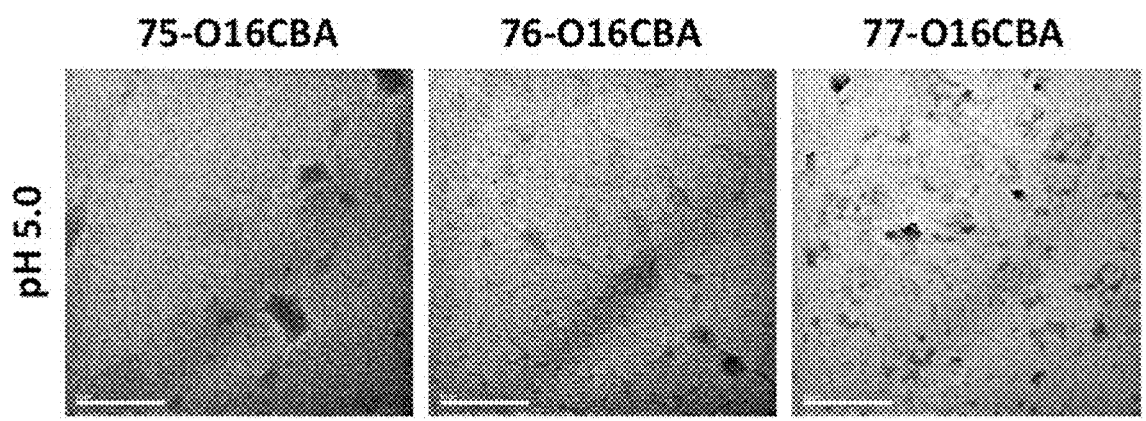
FIG. 13 is a set of additional TEM images of 75-, 76-, and 77-O16CBA LNPs after 24 h incubation under pH 5.0.

After 24 h incubation at pH 5.0, lipidoid nanoparticles were disrupted and amorphous aggregates around 130 nm resulted (FIG. 4A). The same acid-triggered morphological transformations were also observed in 76-O16CBA and 77-O16CBA LNPs with TEM images (FIG. 13). DLS measurements further indicated size variations after acid treatment. The hydrodynamic diameter of 75-O16CBA decreased from 382 nm to 150 nm after 24 h of incubation in pH 5.0 solution (FIG. 4B). Decrease in average hydrodynamic size was also observed for 76- and 77-O16CBA, which was consistent with the TEM observation results. The hydrodynamic size of R-O16CBA measured by DLS was larger than the average size calculated from TEM images. This could be due to the fact that the TEM images were taken under dry status. Following previously reported procedures, a microenvironment polarity-sensitive fluorescent dye (Nile red) was incorporated into the hydrophobic lipidoid bilayer membrane of 75-O16CBA LNPs. Nile red has bright fluorescence emission in the nonpolar environment such as lipidoid bilayer, and reduced fluorescence in polar or aqueous solution. A decrease in fluorescence emission intensity (ca. 54%) and a red-shift in maximum emission peaks (from 619 to 646 nm) of NR/75-O16CBA was observed after 24 h of incubation at pH 5.0 (FIG. 4C). This indicated that the microenvironment variation and nanoparticle dissociation occurred after the acid treatment. Overall, the $^1H$ NMR, MS, TEM, DLS, and fluorescence measurements demonstrated the acid-triggered degradation of R-O16CBA lipidoid molecules as well as the resulting disruption of nanoparticle structures.

Example 4. R-O16CBA LNPs for mRNA Delivery

The possibility of using R-O16CBA molecules as the active lipidoids for intracellular mRNA delivery was explored. In this study, different formulations were prepared. As shown in Table 1, R-O16CBA LNPs contain R-O16CBA only; R-O16CBA-F1 LNPs contain R-O16CBA, cholesterol, and DOPE at a weight ratio of 4/1/1; R-O16CBA-F2 LNPs contain R-O16CBA, cholesterol, and DOPE at a weight ratio of 4/1/4. Cholesterol and DOPE were added because previous studies have shown that these helper lipids can increase the stabilization of nanoparticles, membrane infusion, and cellular internalization.

TABLE 1

Codes and parameters of lipidoid nanoparticle formulations used in this study.

| Code | Weight ratio | | |
|---|---|---|---|
| | Lipidoid | Cholesterol | DOPE |
| R-O16CBA | 4 | 0 | 0 |
| R-O16CBA-F1 | 4 | 1 | 1 |
| R-O16CBA-F2 | 4 | 1 | 4 |

Figure 5:
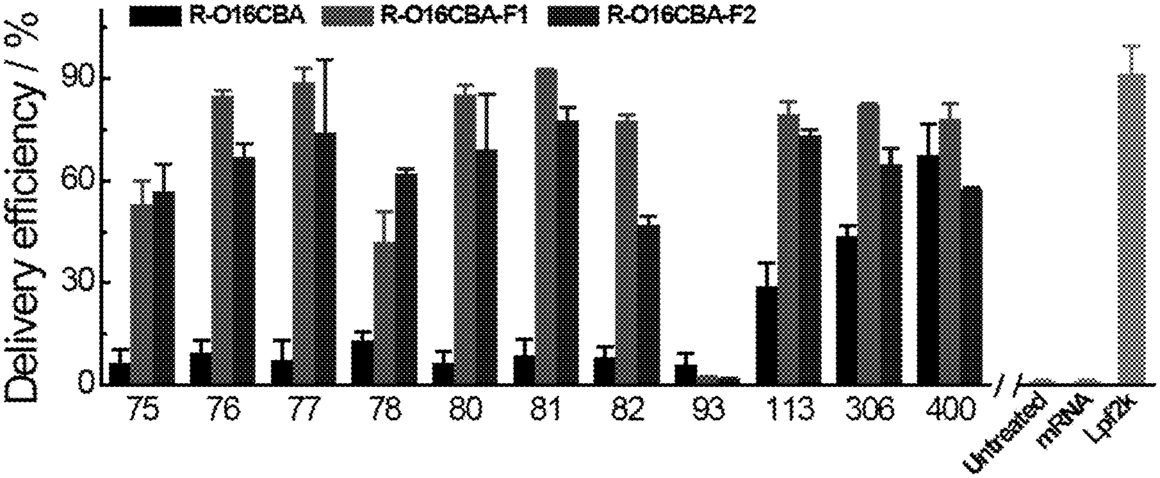
FIG. 5 is a bar graph showing intracellular GFP mRNA delivery efficacies of R-O16CBA LNP formulations (R-O16CBA, R-O16CBA-F1, and R-O16CBA-F2). Lpf2k and naked mRNA were used as positive and negative controls. [R-O16CBA]=7.4 μg/mL; [GFP mRNA]=0.74 g/mL; exposure duration=24 h.

GFP mRNA was loaded into different nanoparticle formulations by mixing mRNA and LNPs in PBS buffer (R-O16CBA/mRNA=10/1; weight ratio). Most of the combinatial LNPs showed great stability during storage. Furthermore, the stability of LNPs can be further improved by adding small- and macromolecular excipients (cholesterol, DOPE, PEG-DSPE etc.) into the formulations. It should be noted that in all of the following studies, freshly prepared LNPs were used unless otherwise noted. The mRNA and LNPs were added to HeLa cells, and the delivery efficiencies were determined using flow cytometry after 24 h of incubation ([R-O16CBA]=7.4 g/mL; [GFP mRNA]=0.74 μg/mL; exposure duration=24 h). Intracellular mRNA delivery efficiency was represented by the percentage of GFP+ cells. Commercially available cationic transfection reagent, Lpf2k, was used as a positive control. Untreated HeLa cells and HeLa cells treated with naked GFP mRNA were used as negative controls. As shown in FIG. 5, both untreated cells and naked mRNA-treated cells induced a negligible percentage of GFP+ HeLa cells (<1%). On the other hand, Lpf2k was highly efficient in mRNA delivery as ~91% GFP+ cells were recorded.

It was discovered that the neutral helper lipids (cholesterol and DOPE) in R-O16CBA formulations played an essential role in mRNA delivery. Without helper lipids, the delivery efficiencies were rather low, as eight of the LNP formulations (75-O16CBA and 76-O16CBA etc.) had efficiencies below 15%. Two lipidoid nanoparticles, 113-O16CBA and 306-O16CBA, induced 29% and 44% GFP+ cells respectively, while the most active 400-O16CBA induced 68% GFP+ cells. The outperformance of lipidoids with more than two tails (113-, 306-, and 400-O16CBA) compared to lipidoids with two tails (75-O16CBA etc.) for nucleic acid delivery is consistent with previous reports and merits further study.

The addition of helper lipids greatly improved LNP delivery efficacy, with multiple LNPs achieving GFP expression comparable to that of Lpf2k. In the library of R-O16CBA-F1 formulations, all LNPs, except for 93-O16CBA-F1 (~2% GFP+ cells), showed higher efficacies than their corresponding R-O16CBA formulations. Nine of the R-O16CBA-F1 formulations had >50% delivery efficiency, with 81-O16CBA-F1 being the highest in producing ~93% GFP+ cells. Other top formulations such as 76-, 77-, 113-, 306-, and 400-O16CBA-F1 induced delivery efficacies of 78-83%.

The effects of increasing the amount of helper lipids on mRNA delivery was then investigated. Formulations with R-O16CBA/cholesterol/DOPE at a weight ratio of 4/1/4 were fabricated and tested (R-O16CBA-F2). As shown in FIG. 5, except for the 93-O16CBA-F2 and 400-O16CBA-F2, all other LNPs had higher efficacies than R-O16CBA. Compared to the R-O16CBA-F1 LNPs, the delivery efficacies of R-O16CBA-F2 were slightly lower (except for 75- and 78-O16CBA-F2). 81-O16CBA-F2 was determined to be the most efficient in this formulated library as ~78% GFP+ cells were recorded. Once again, 113-, 306-, and 400-O16CBA-F2 were still among the top LNPs, as their delivery efficacies were determined to be 57-73%.

Overall, the addition of helper lipids can improve most LNP delivery efficacies. R-O16CBA-F2 LNPs, which had higher DOPE content, had comparable or slightly lower efficacies than R-O16CBA-F1 LNPs. In addition, 81-O16CBA-F1 and -F2 were determined to be the most efficient in the two formulation libraries, and three-tailed LNPs performed well both with and without helper lipids.

Example 5. Cytotoxicity Test

Figure 6:
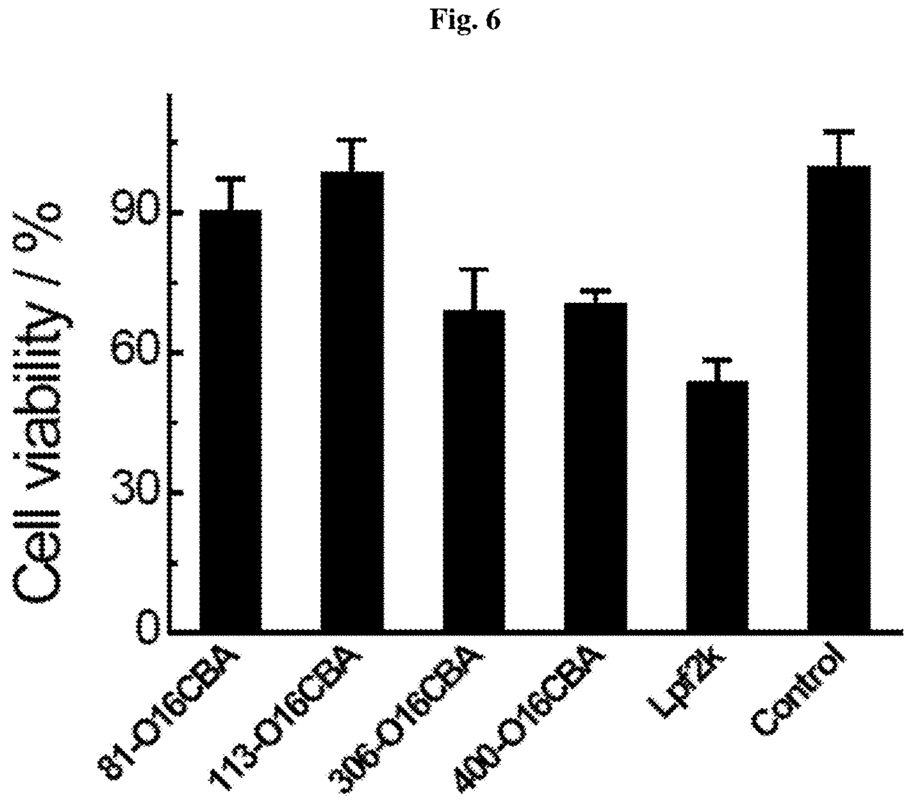
FIG. 6 is a bar graph showing cytotoxicity test of R-O16CBA LNPs and Lpf2k ([lipdoid]=7.4 μg/mL; exposure duration=24 h). Untreated cells were used as negative controls.

As discussed above, some of the R-O16CBA formulations achieved comparable mRNA delivery efficacies to that of the commercial reagent Lpf2k. Besides efficacy, the biocompatibility of carriers was also examined. Although Lpf2k is highly efficient, previous research indicated it is also toxic. In this context, the cytotoxicities of four successful R-O16CBA LNPs, namely one two-tailed lipidoid (81-O16CBA) and three multiple-tailed lipidoids (113-, 306-, and 400-O16CBA), were tested using the MTT assay ([lipidoid]=7.4 μg/mL; exposure duration=24 h). The addition of helper lipids like cholesterol and DOPE would result in very similar to slightly lower cytotoxicity of the formulations, which is reasonable considering the excellent cell compatibility of cholesterol and DOPE etc. As shown in FIG. 6, although Lpf2k is highly efficient for mRNA delivery, it is also rather toxic, as only ~53% of cells were viable after delivery. On the other hand, the newly developed R-O16CBA LNPs were less toxic under the same conditions. 306- and 400-O16CBA had ~70% cell viabilities, and 81- and 113-O16CBA had >90% cell viabilities.

INCORPORATION BY REFERENCE

All of the U.S. patents, and U.S. and PCT published patent applications cited herein are hereby incorporated by reference.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

We claim:

1. A compound of formula I:

(I)

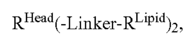

$R^{Head}(\text{-Linker-}R^{Lipid})_2$, or a pharmaceutically acceptable salt thereof, wherein $R^{Head}$ is

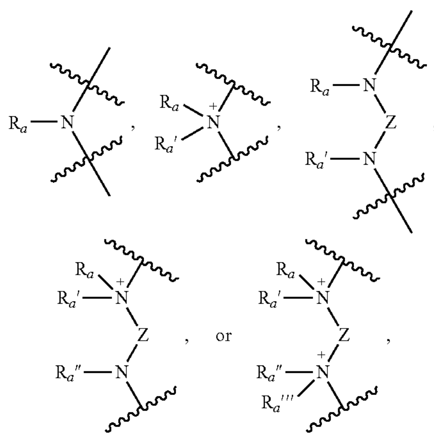

, , , , or , $R^a$, $R^{a'}$, $R^{a''}$, and $R^{a'''}$ independently are H, $C_1$-$C_{20}$ alkyl, $C_2$-$C_{20}$ alkenyl, $C_2$-$C_{20}$ alkynyl, $C_3$-$C_{20}$ cycloalkyl, $C_1$-$C_{20}$ heteroalkyl, (heterocyclyl)$C_1$-$C_{20}$alkyl, aryl, heteroaryl, or

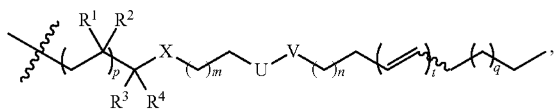

, wherein $R^a$ and $R^{a'}$ or $R^{a''}$, and $R^{a'''}$ are not both

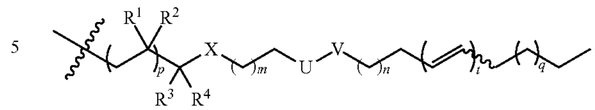

;

Z is a $C_1$-$C_{20}$ bivalent aliphatic radical, a $C_1$-$C_{20}$ bivalent heteroaliphatic radical, a bivalent aryl radical, or a bivalent heteroaryl radical;

Linker has a structure represented by formula II:

(II)

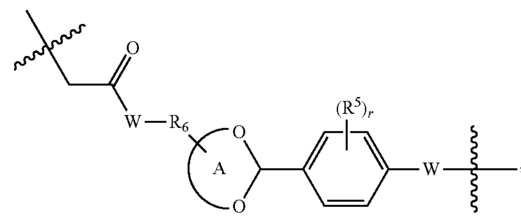

, wherein

W is O or NH;

each of $R^5$ independently is hydrogen, halogen, nitro, cyano, amino, hydroxyl, alkoxy, alkylthio, alkyl, alkenyl, alkynyl, aralkyl, heteroaralkyl, carbocycle, heterocyclyl, aryl, or heteroaryl;

r is an integer selected from 0 to 4;

A is an optionally substituted 5- to 8-membered heterocycle;

$R^6$ is absent; or $R^6$ is alkylene or alkenylene;

each instance of $R^{Lipid}$ independently is $C_1$-$C_{20}$ alkyl, $C_2$-$C_{20}$ alkenyl, $C_2$-$C_{20}$ alkynyl,

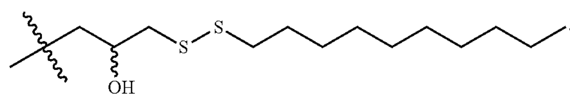

,

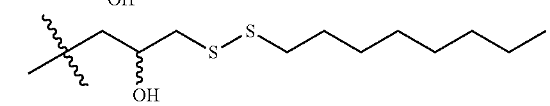

,

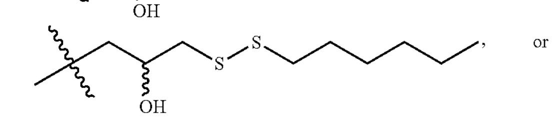

, or

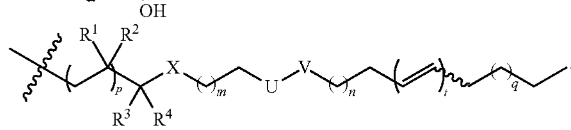

, wherein:

$R^1$ and $R^2$ independently are H, OH, $NHR^{30}$, or SH;

$R^3$ and $R^4$ are both H; or $R^3$ and $R^4$ are taken together to form an oxo (=O) group;

X is $CH_2$, O, $NR^{30}$, or S;

$R^{30}$ is H, $C_{1-6}$ alkyl, $C_{1-6}$ alkenyl, or $C_{1-6}$ alkynyl;

U and V independently are S, Se, O, or $CH_2$;

m is an integer selected from 1 to 3;

n is an integer selected from 1 to 14;

p is 0 or 1;

q is an integer selected from 1 to 10; and t is 0, 1, or 2.

2. The compound of claim 1, wherein $R^{Head}$ is selected from the group consisting of

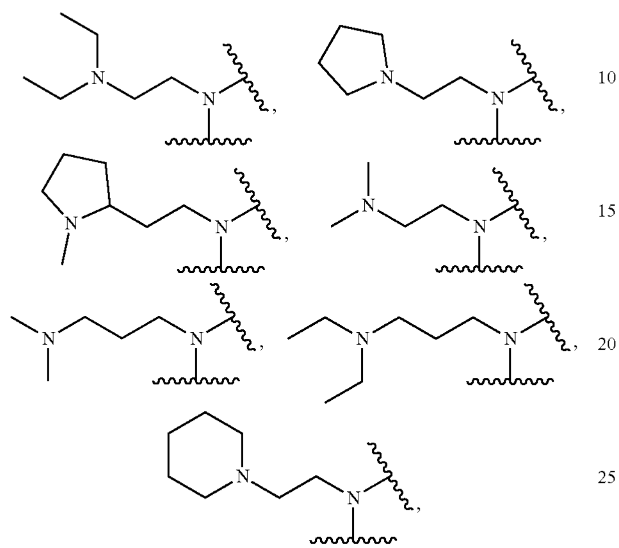

-continued

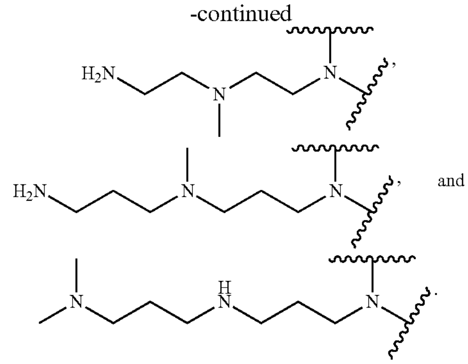

and

3. The compound of claim 1, wherein each instance of $R^{Lipid}$ independently is $C_1$-$C_{20}$ alkyl, $C_2$-$C_{20}$ alkenyl, or $C_2$-$C_{20}$ alkynyl.

4. The compound of claim 1, wherein A is substituted with halogen, nitro, cyano, amino, hydroxyl, alkoxy, alkylthio, alkyl, alkenyl, alkynyl, aralkyl, heteroaralkyl, carbocyclyl, heterocyclyl, aryl, or heteroaryl.

5. The compound of claim 1, wherein each instance of $R^{Lipid}$ independently is selected from the group consisting of n-pentyl, n-hexyl, n-heptyl, n-octyl,

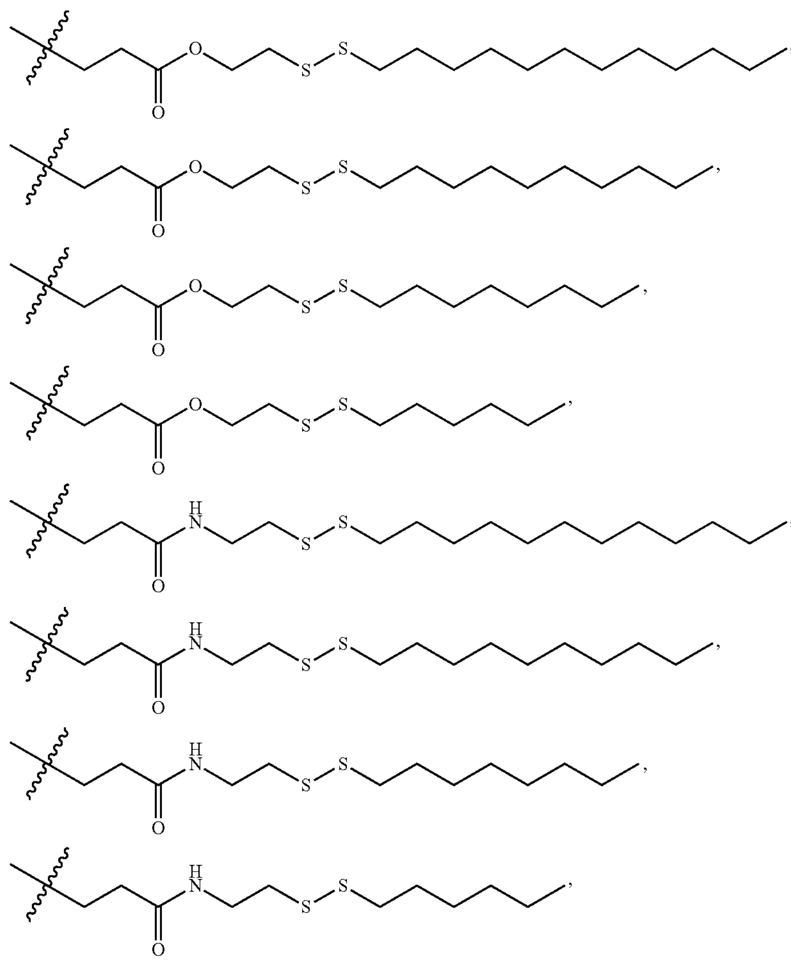

-continued
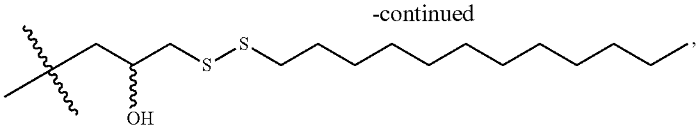,
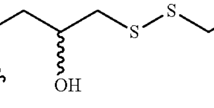,
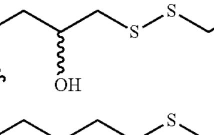,
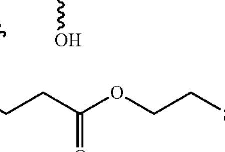,
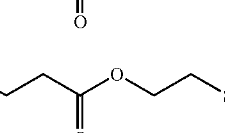,
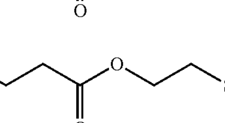,
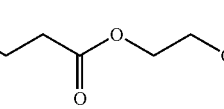,
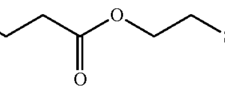,
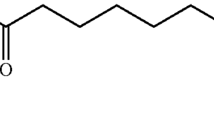, and
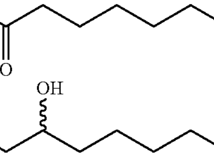.
6. The compound of claim 1, wherein A is unsubstituted.
7. A compound of formula III:
(III)
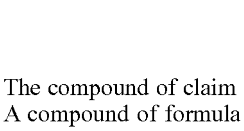
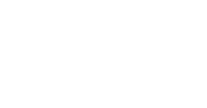
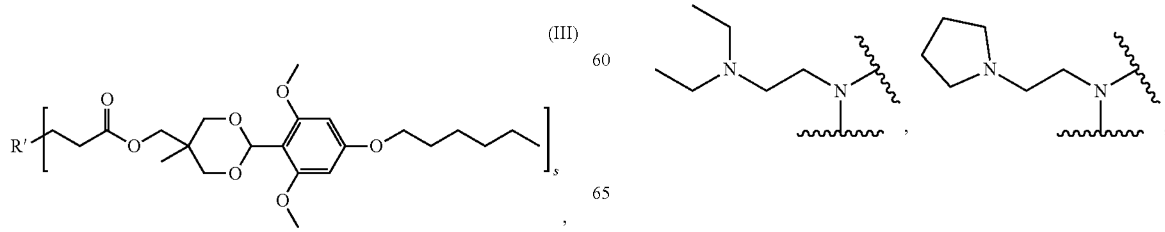,
wherein R′ is
-continued
,
, -continued

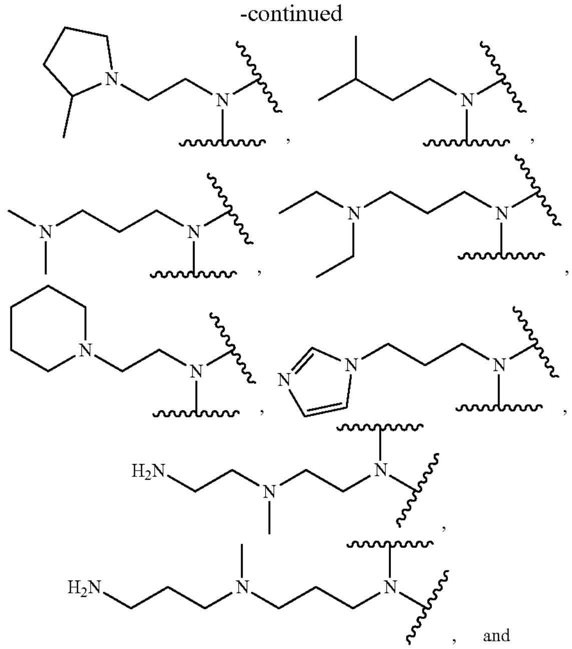

and

-continued

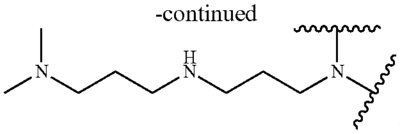

;

and s is 2.

8. A lipidoid nanoparticle, comprising a compound of claim 1.

9. The lipidoid nanoparticle of claim 8, wherein the lipidoid nanoparticle further comprises cholesterol.

10. The lipidoid nanoparticle of claim 9, wherein the weight ratio of the compound to the cholesterol is about 2:1 to about 8:1.

11. The lipidoid nanoparticle of claim 9, wherein the weight ratio of the compound to the cholesterol is about 4:1.

12. The lipid nanoparticle of claim 9, wherein the lipidoid nanoparticle further comprises DOPE; and the weight ratio of the compound to the DOPE is about 4:1 to about 1:1.

13. The lipidoid nanoparticle of claim 8, wherein the lipidoid nanoparticle further comprises DOPE, DSPC, DOPC, or DMG-PEG2K or a combination thereof; wherein DSPC has the structure:

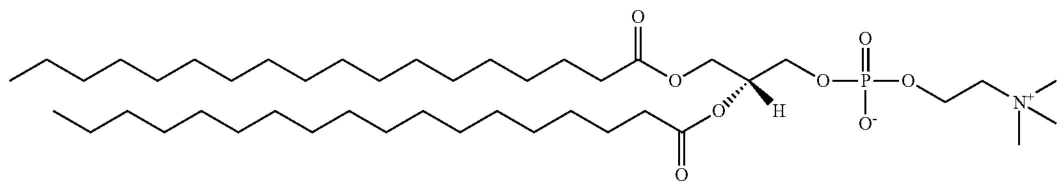

;

DOPE has the structure:

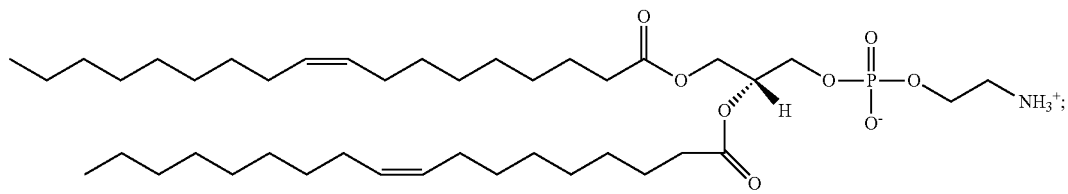

;

DOPC has the structure:

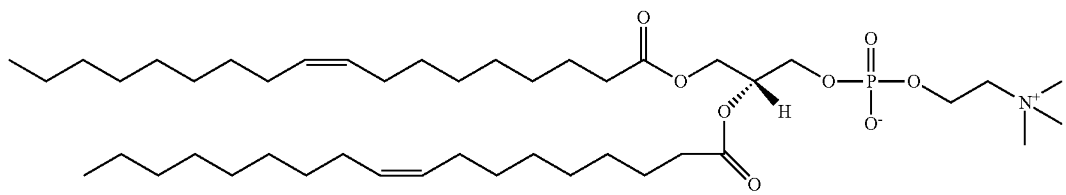

,

DMG-PEG2K has the structure:

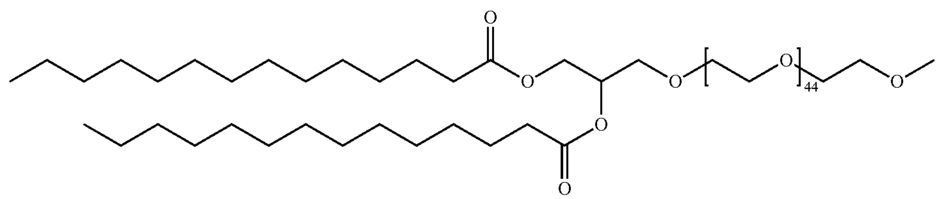

14. The lipidoid nanoparticle of claim 8, further comprising an mRNA.

15. The lipidoid nanoparticle of claim 8, further comprising a small molecule.

16. The lipidoid nanoparticle of claim 15, wherein the small molecule is an antifungal agent or a chemotherapeutic agent.

17. The lipidoid nanoparticle of claim 16, wherein the small molecule is selected from the group consisting of bortezomib, imatinib, gefitinib, erlotinib, afatinib, osimertinib, dacomitinib, daunorubicin hydrochloride, cytarabine, fluorouracil, irinotecan hydrochloride, methotrexate, paclitaxel, vincristine sulfate, epirubicin, docetaxel, cyclophosphamide, carboplatin, lenalidomide, ibrutinib, abiraterone acetate, enzalutamide, pemetrexed, palbociclib, nilotinib, everolimus, ruxolitinib, epirubicin, pirarubicin, idarubicin, valrubicin, amrubicin, bleomycin, phleomycin, dactinomycin, mithramycin, streptozotocin, pentostatin, mitosanes mitomycin C, enediynes calicheamycin, glycosides rebeccamycin, macrolide lactones epothilones, ixabepilone, pentostatin, salinosporamide A, vinblastine, vincristine, etoposide, teniposide, vinorelbine, docetaxel, camptothecin, hycamtin, pederin, theopederins, annamides, trabectedin, aplidine, and ecteinascidin 743 (ET743).

18. The lipidoid nanoparticle of claim 16, wherein the small molecule is Amphotericin B or Doxorubicin.

19. The lipidoid nanoparticle of claim 8, wherein the lipidoid nanoparticle has a particle size of about 200 nm to about 500 nm.

20. A pharmaceutical composition, comprising a lipidoid nanoparticle of claim 8, and one or more pharmaceutically acceptable carriers or excipients.

* * * * *